United States Patent
Tavanei et al.

(10) Patent No.: US 11,978,207 B2
(45) Date of Patent: May 7, 2024

(54) ORAL CARE BASED DIGITAL IMAGING SYSTEMS AND METHODS FOR DETERMINING PERCEIVED ATTRACTIVENESS OF A FACIAL IMAGE PORTION

(71) Applicant: The Procter & Gamble Company, Cincinnati, OH (US)

(72) Inventors: Amirhossein Tavanei, Mason, OH (US); Matthew Lloyd Barker, Mason, OH (US); Faiz Feisal Sherman, Mason, OH (US); Sherrie Lee Kinderdine, Mason, OH (US); Scott Alan Hayes, Cincinnati, OH (US); David Anthony Hengehold, Florence, KY (US); Yanyan He, Beijing (CN); Yumeng Ouyang, Beijing (CN); Jiahui Li, Beijing (CN); Nataliya Gurich, Cincinnati, OH (US); Ming Qi, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 253 days.

(21) Appl. No.: 17/337,503

(22) Filed: Jun. 3, 2021

(65) Prior Publication Data
US 2022/0398731 A1 Dec. 15, 2022

(51) Int. Cl.
*G06T 7/00* (2017.01)
*A61B 1/24* (2006.01)
(Continued)

(52) U.S. Cl.
CPC ......... *G06T 7/0014* (2013.01); *G06Q 10/083* (2013.01); *G06Q 30/0631* (2013.01);
(Continued)

(58) Field of Classification Search
CPC ......... G06T 7/0014; G06T 2207/30036; G06T 2207/30201; G06V 40/171; G06V 40/175; G16H 50/20; A61B 1/24
See application file for complete search history.

(56) References Cited

U.S. PATENT DOCUMENTS 8,041,076 B1 10/2011 Bourdev
8,073,212 B2 * 12/2011 Gerlach ............... A61B 5/0088
382/128
(Continued)

FOREIGN PATENT DOCUMENTS

CN 10484066 B 1/2012
CN 110472489 A 11/2019
(Continued)

OTHER PUBLICATIONS

PCT Supplementary Search Report and Written Opinion for PCT/CN2020/094342 dated Jul. 27, 2022, 14 pages.
(Continued)

*Primary Examiner* — Wesley J Tucker
(74) *Attorney, Agent, or Firm* — Elizabeth A. Conklin

(57) ABSTRACT

Oral care based imaging computer-implemented systems and methods for determining perceived attractiveness of a facial image portion of at least one person depicted in a digital image. The method has the following steps:
a) obtaining a digital image comprising at least one oral feature of at least one person, wherein the digital image includes a facial image portion of the at least one person, the facial image portion having both positive and negative attributes as defined by pixel data of the digital image;
b) analyzing the facial image portion;
c) generating an Attractiveness Score indicative of a perceived attractiveness of the facial image portion based on the analyzed facial image portion in the obtained digital image;
(Continued)

d) further generating an image description that identifies at least one area in said facial image portion based on the Attractiveness Score; and e) presenting the image description to a use.

23 Claims, 18 Drawing Sheets

(51) Int. Cl.
    *G06Q 10/083*     (2023.01)
    *G06Q 30/0601*     (2023.01)
    *G06V 40/16*     (2022.01)
    *G16H 50/20*     (2018.01)

(52) U.S. Cl.
    CPC .......... *G06V 40/166* (2022.01); *G06V 40/171* (2022.01); *G06V 40/175* (2022.01); *G16H 50/20* (2018.01); *A61B 1/24* (2013.01); *G06T 2207/30036* (2013.01); *G06T 2207/30201* (2013.01)

(56) References Cited

U.S. PATENT DOCUMENTS

| | | | | |
|---|---|---|---|---|
| 9,020,236 | B2* | 4/2015 | Wang | G06T 7/0012 |
| | | | | 382/132 |
| 2005/0196039 | A1 | 9/2005 | Bengel et al. | |
| 2009/0074679 | A1* | 3/2009 | Silverman | A61Q 11/02 |
| | | | | 424/53 |
| 2009/0257654 | A1* | 10/2009 | Roizen | A45D 44/005 |
| | | | | 705/2 |
| 2011/0014351 | A1* | 1/2011 | Reider | G16H 10/20 |
| | | | | 53/473 |
| 2012/0134558 | A1* | 5/2012 | Sienkiewicz | A61C 19/00 |
| | | | | 382/128 |
| 2013/0243338 | A1 | 9/2013 | Palmer | |
| 2015/0213622 | A1* | 7/2015 | Abdulwaheed | G06T 7/90 |
| | | | | 382/128 |
| 2015/0351638 | A1* | 12/2015 | Amato | A61B 6/14 |
| | | | | 433/215 |
| 2017/0172418 | A1* | 6/2017 | Munro | A61C 9/0053 |
| 2017/0270593 | A1 | 9/2017 | Sherman et al. | |
| 2019/0313963 | A1* | 10/2019 | Hillen | G06V 10/764 |
| 2019/0349518 | A1* | 11/2019 | Abdulwaheed | G06V 20/10 |
| 2020/0042769 | A1* | 2/2020 | Yan | G06T 3/40 |
| 2020/0187851 | A1* | 6/2020 | Offenbacher | G16H 50/30 |
| 2021/0073709 | A1* | 3/2021 | Shaw | G16H 50/70 |
| 2022/0076000 | A1* | 3/2022 | Yang | G06V 20/597 |
| 2023/0215063 | A1* | 7/2023 | Gadiyar | G06V 10/751 |
| | | | | 382/128 |
| 2023/0222750 | A1* | 7/2023 | Querbes | G06T 7/70 |
| | | | | 345/420 |

FOREIGN PATENT DOCUMENTS

| | | |
|---|---|---|
| CN | 111091040 A | 5/2020 |
| CN | 111191137 A | 5/2020 |

OTHER PUBLICATIONS

Liu Shu et al. "Advances in computational facial attractiveness methods", Aug. 11, 2016, p. 31.

Zhao Jian et al. "Data-Driven Research on the Matching Degree of Eyes, Eyebrows and Face Shapes", vol. 10, Jul. 2, 2019, p. 11.

PCT Search Report and Written Opinion for PCT/CN2020/094342 dated Mar. 3, 2021, 7 pages.

* cited by examiner

ORAL CARE BASED DIGITAL IMAGING SYSTEMS AND METHODS FOR DETERMINING PERCEIVED ATTRACTIVENESS OF A FACIAL IMAGE PORTION

TECHNICAL FIELD

The present invention relates to oral care based digital imaging systems and methods for processing information associated with image data such as a digital image, a video defined by a sequence of digital images (also known as frames). In particular, the present invention relates to a system and a method for determining perceived attractiveness of a facial image portion of at least one person depicted in a digital image.

BACKGROUND

Attractiveness plays a central role in human preoccupation with self-image as seen in the proliferation of bodily practices aimed at constantly improving the body and its influence on social relationships. Visual cues can strongly influence the attractiveness of a person in the perception of one self or by a population of people. One visual cue is facial appearance of a person and concepts used to describe the facial appearance can influence whether a person is perceived to be attractive relative to another person or a population of people. However, attractiveness is highly subjective. Consumers also seek to improve their attractiveness through the use of a variety of consumer products including but limited to oral care products, dental treatments, skin care products, or the like. However, it is difficult to improve the attractiveness without prior knowledge as to what is impacting attractiveness.

U.S. Pat. No. 6,571,003B1 describes an apparatus and method for displaying information associated with a plurality of skin defects and in particular for determining and displaying the location of one or more analysis areas and defect areas associated with a digital image of human skin and for determining the severity of these defects as well as displaying an improvement and/or worsening to the defect areas. U.S. Pat. No. 8,073,212 describes methods and products for analyzing gingival tissues. U.S. Pat. No. 10,405,754 describes standardized oral health assessment and scoring using digital images.

Accordingly, there is a need for a method of determining perceived attractiveness of a person's appearance, which can then improve the person's ability to take steps or make an informed decision to improve perceived attractiveness of his or her facial appearance.

SUMMARY

The present invention relates to a computer-implemented method for determining perceived attractiveness of a facial image portion of at least one person depicted in a digital image, the method comprising the steps of:
  a) obtaining a digital image of at least one person, wherein the digital image comprises a facial image portion of the at least one person, wherein the facial image portion has both positive and negative attributes;
  b) analyzing the facial image portion;
  c) generating an Attractiveness Score indicative of the perceived attractiveness of the facial image portion based on the analyzed facial image portion;
  d) further generating an image description that identifies at least one area in said facial image portion based on the Attractiveness Score; and
  e) presenting the image description to a user.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate various embodiments described herein, and together with the description serve to explain the principles and operations of the claimed subject matter.

DETAILED DESCRIPTION

Figure 1:
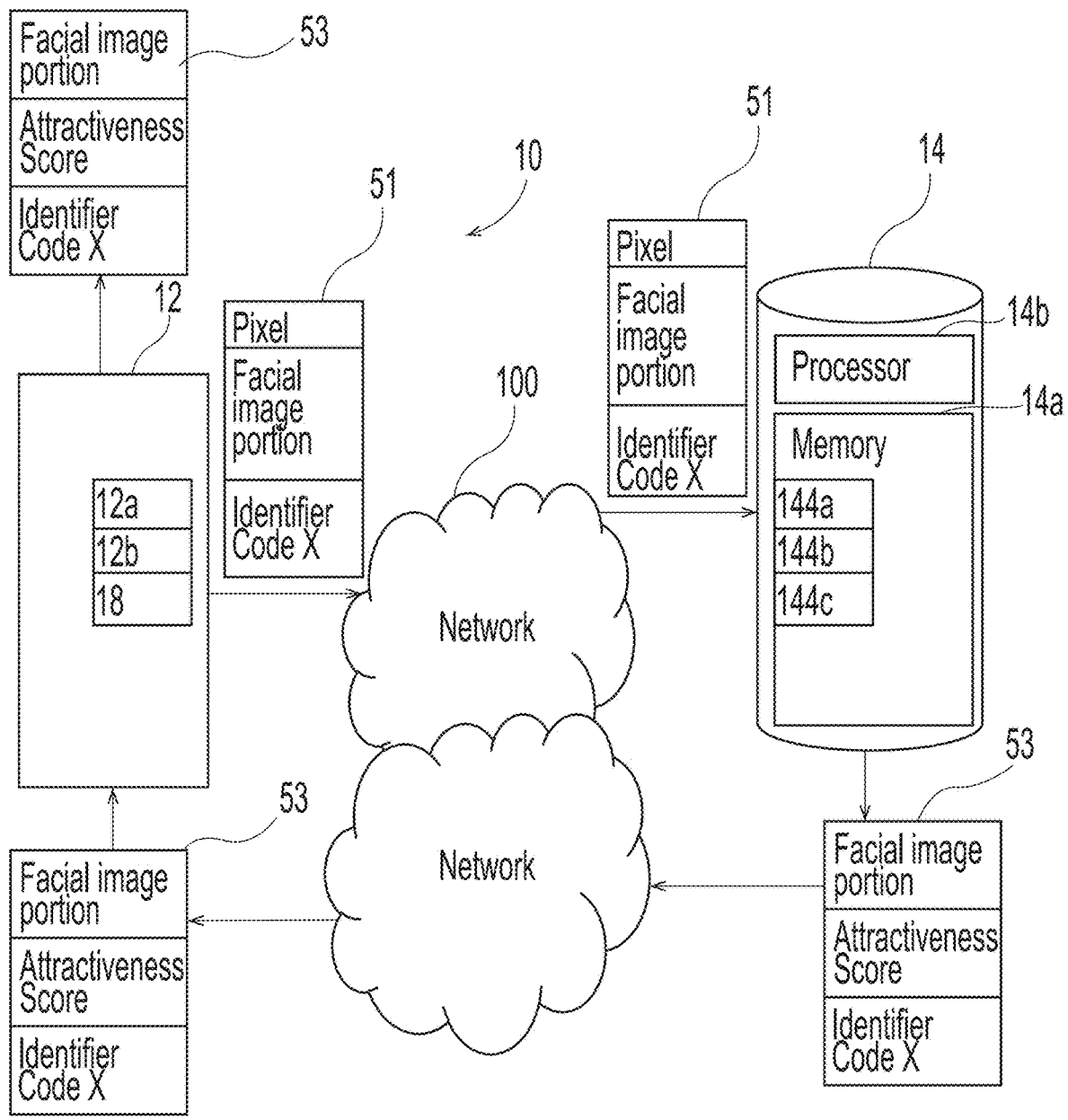
FIG. 1 is a diagram illustrating an exemplary system for determining perceived attractiveness of a facial image portion over a network according to the present invention.

The present invention relates to a method, apparatus and system for determining perceived attractiveness of a facial image portion in a digital image, and a graphical user interface for visualizing perceived attractiveness. A facial image portion is of a person, and may comprise one or more facial features, a facial expression, or combinations thereof. Facial features may include nose, mouth, eyes, facial skin, teeth, gum. Facial expression may be a smile.

As described herein, the perceived attractiveness of a facial image portion provides a benefit as it is multi-faceted, i.e. a perceived attractiveness provides both visual facial features which appear healthy (hereinafter "healthy-looking facial features") and visual facial features which appear to have problems or that appear to be less healthy than the healthy-look facial features. In particular, perceived attractiveness is impacted by positive attributes and negative attributes present in a facial image portion depicted in a digital image. Positive attributes may comprise whiteness of teeth, pinkness of gums, smoothness of teeth surfaces or positive appearances of the teeth or gums. Negative attributes may comprise teeth stains, gum redness, swollen gums or the like.

Prior to describing the present invention in detail, the following terms are defined and terms not defined should be given their ordinary meaning as understood by a skilled person in the relevant art.

"Perceived attractiveness" as used herein means a quality of a facial image portion of a person depicted in a digital image as perceived by a population of people (hereinafter "population") that appeals to the population. The population may include professionals, industry experts, consumers or combinations thereof. Perceived attractiveness may include but is not limited to, an affinity or a liking for a person having a facial image portion depicted in the digital image, attractiveness of a facial image portion in the context of a person having the facial image portion includes an attribute of the facial image portion that the person is motivated to do something to improve attractiveness of the facial image portion.

"Person" as used herein means a human being depicted in a digital image.

"Facial image portion" as used herein means any concept, digital image, or image digital portion based on detection of one of a face of a person depicted or more faces of people, including but not limited to one or more facial features, one or more oral features, a facial expression, or combinations thereof, for example, as determined or detected by the pixel data or otherwise pixels of one or more corresponding digital image(s).

"Facial feature" as used herein is an element of a face, and may include but is not limited teeth, gum, nose, mouth, eyes, facial skin, including such features as determined or detected by the pixel data or otherwise pixels of one or more corresponding digital image(s).

"Facial expression" as used herein is one or more motions or positions of the muscles beneath the skin of the face, and may include but is not limited to a smile.

"Smile" as used herein is made up of teeth and/or gums but does not include the lips of the mouth, including, for example, as determined or detected by the pixel data or otherwise pixels of one or more corresponding digital image(s).

"Oral feature" as used herein is an element of the mouth, and may include but is not limited to oral cavity soft tissue, gums, teeth, including, for example, as determined or detected by the pixel data or otherwise pixels of one or more corresponding digital image(s).

"Attractiveness Score (吸引力指数)" as used herein means a probability value indicative of how appealing a facial image portion of a person depicted in a digital image is to a population of people (hereinafter "population") based on positive and negative attributes of the facial image portion (e.g. teeth). The probability value may be determined by a model constructed by a machine learning system trained by a training dataset, wherein the training dataset comprises (i) a plurality of simulated images of a facial image portion (e.g., teeth) comprising positive (white areas) and negative (stained areas) attributes; and (ii) an associated class definition (e.g. facial staining) based on positive and negative attributes. The probability value may be a numerical value indicative of a perceived attractiveness of a facial image portion depicted in a digital image calculated by the system herein (an attractiveness model is described hereinafter as an example of a machine learning system), based on the positive and negative attributes of the facial image portion in the digital image.

An attractiveness model may be based on training data obtained from the raw consumer choice data by estimating the part-worth utilities for the eight attributes' main effects and limited interaction terms via hierarchical bayes (HB) estimation. The Attractiveness Score for any particular training image could then be calculated from the sum of the part-worth utilities across the chosen attribute levels.

"Attribute" as used herein means a measurable property of the facial image portion.

"Cosmetic dental attribute" as used herein means all cosmetic dental attributes that provide an oral health effect on an area of the oral cavity or impact appearance and/or feel thereof. Some non-limiting examples of a cosmetic dental attribute may include gum inflammation/redness, gum firmness, gum bleeding, gum sensitivity, yellowness, lightness, front surface staining, interproximal (IP) staining in between adjacent teeth, marginal staining (around the gum line), opacity, shine.

"Convolutional neural network" is a type of feed-forward artificial neural network where the individual neurons are tiled in such a way that they respond to overlapping regions in the visual field.

"Oral care product" as used herein, refers to a product that includes an oral care active and regulates and/or improves a cosmetic dental attribute condition. An oral care product may include but is not limited to, toothpaste, mouth rinse, dental floss, whitening strips, or the like.

"Digital image" as used herein, refers to a digital image formed by pixels in an imaging system including but not limited to standard RGB, or the like and under images obtained under different lighting conditions and/or modes. Non-limiting examples of a digital image include color images (RGB), monochrome images, video, multispectral image, hyperspectral image or the like. Non-limiting light conditions include white light, blue light, UV light, IR light, light in a specific wavelength, such as for example light source emitting lights from 100 to 1000 nm, from 300 to 700 nm, from 400 to 700 nm or different combinations of the upper and lower limits described above or combinations of any integer in the ranges listed above. A digital image may be a single photograph or a single frame in a series of frames defining a video.

"Image obtaining device" as used herein, refers to a device configured for obtaining images, including but not limited to a digital camera, a photo scanner, a computer readable storage medium capable of storing digital images, and any electronic device including picture taking capabilities.

"User" as used herein refers to a person who uses at least the features provided herein, including, for example, a device user, a product user, a system user, and the like.

"Module" as used herein can be associated with software, hardware, or any combination thereof. In some implementations, one or more functions, tasks, and/or operations of modules can be carried out or performed by software routines, software processes, hardware, and/or any combination thereof.

"Heat map" as used herein refers to a graphical representation of image data comprised in a digital image in which portions of the facial image portion depicted in the digital image are visually highlighted to identify targets of analysis to be presented in the image description. For example, if the target of analysis is a negative attribute of the facial image portion, an area of the facial image portion which comprises the negative attribute will be visualized.

"Treat", "Treating" as used herein refers to providing a product recommendation, customized instructions, use of a recommended product for improving perceived attractiveness of a facial image portion of a subject depicted in a digital image. The subject is a person.

In the following description, the system described is a system 10 for determining perceived attractiveness of a smile 521 of a person depicted in a digital image 51. Accordingly, the apparatus 14 described is an apparatus 14 for determining perceived attractiveness of a smile 521 of a person, and a system for providing a product recommendation to improve perceived attractiveness of a smile 521 of a person depicted in a digital image is also described. Accordingly, positive and negative attributes of a smile 521 relate to cosmetic dental attributes as described hereinbefore, i.e. all cosmetic dental attributes that provide an oral health effect on an area of the oral cavity or impact appearance and/or feel thereof. However, it is contemplated that the apparatus and the method may be configured for use in a variety of applications to determine perceived attractiveness of other facial image portions, wherein the facial image portion is one or more facial features including but not limited to the nose, skin, lips, eyes, combinations thereof.

System

FIG. 1 is a schematic diagram illustrating a system 10 for determining perceived attractiveness of a facial image portion 52 of a person depicted in a digital image 51 according to the present invention. In an exemplary embodiment, the system 10 is a cloud-based system configured for use anywhere, such as for example, through a portable electronic device 12 comprising an image obtaining device 18 and a display (not shown). The portable electronic device 12 may be connected to an apparatus 14 for generating for display on a display, a graphical user interface for visualizing perceived attractiveness of a facial image portion through a network 100. However, it is contemplated that the system 10 may be configured as a stand-alone system. It is further contemplated that the portable electronic device 12 may be a touch sensitive display.

The system 10 may include a network 100, which may be embodied as a wide area network (such as a mobile telephone network, a public switched telephone network, a satellite network, the internet, etc.), a local area network (such as wireless-fidelity, Wi-Max, ZigBee™, Bluetooth™, etc.), and/or other forms of networking capabilities. Coupled to the network 100 are a portable electronic device 12, and an apparatus 14 for generating for display on a display, a graphical user interface 30 (see FIG. 2A) for visualizing perceived attractiveness. The apparatus 14 is remotely located and connected to the portable electronic device 12 through the network 100. The network 100 may be used to acquire digital images from the portable electronic device 12 and transmitting the digital images to the apparatus 14 to be used in the method 200 according to the present invention described hereinafter with respect to FIG. 7. An input device 12a may be coupled to or integral with the portable electronic device 12 for receiving a user input for initiating the processor 14b. The portable electronic device 12 may comprise an output device 12b for presenting the image description 53 for the facial image portion 52 depicted in the digital image 51. The input device 12a may include but is not limited to a mouse, a touch screen display, or the like. The output device 12b may include but is not limited to a touch screen display, a non-touch screen display, a printer, audio output devices such as for example, speakers.

The portable electronic device 12 may be a mobile telephone, a tablet, a laptop, a personal digital assistant and/or other computing device configured for capturing, storing, and/or transferring a digital image such as a digital photograph. Accordingly, the portable electronic device 12 may include an image obtaining device 18 such as a camera integral with the device 12 for obtaining images and an output device 12*b* for displaying the images. The portable electronic device 12 may also be configured for communicating with other computing devices via the network 100. The apparatus 14 may include a non-transitory computer readable storage medium 14*a* (hereinafter "storage medium"), which stores image obtaining logic 144*a*, image analysis logic 144*b* and graphic user interface (hereinafter "GUI") logic 144*c*. The storage medium 14*a* may comprise random access memory (such as SRAM, DRAM, etc.), read only memory (ROM), registers, and/or other forms of computing storage hardware. The image obtaining logic 144*a*, image analysis logic 144*b* and the GUI logic 144*c* define computer executable instructions. A processor 14*b* is coupled to the storage medium 14*a*, wherein the processor 14*b* is configured to, based on the computer executable instructions, for implementing a method 200 for determining perceived attractiveness of a facial image portion of a person or persons in depicted in a digital image 51 according to the present invention as described herein after with respect to FIGS. 2 to 4 and the flowchart of FIG. 5.

Figure 2:
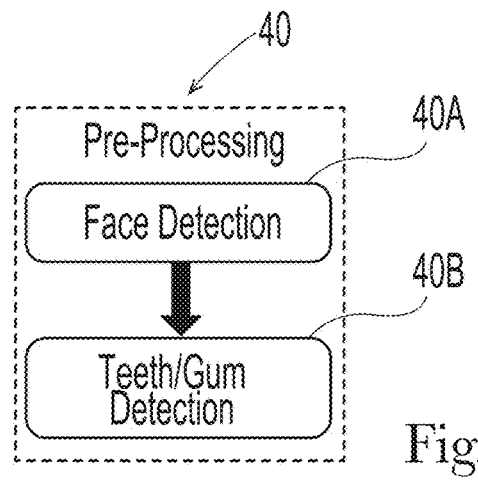
FIG. 2 is a diagram illustrating an exemplary functional block diagram associated with detecting a facial image portion according to the present invention.

FIG. 2 is a diagram illustrating an exemplary functional block diagram of a facial image portion pre-processing module 40 containing image obtaining logic 144*a* for obtaining a digital image 51 comprising a facial image portion 52 according to the present invention. The pre-processing module 40 may comprise a first pre-processing sub-module 40A for detecting the facial image portion 52 and a second pre-processing sub-module 40B for detecting one or more features which define the facial image portion 52.

Figure 3:
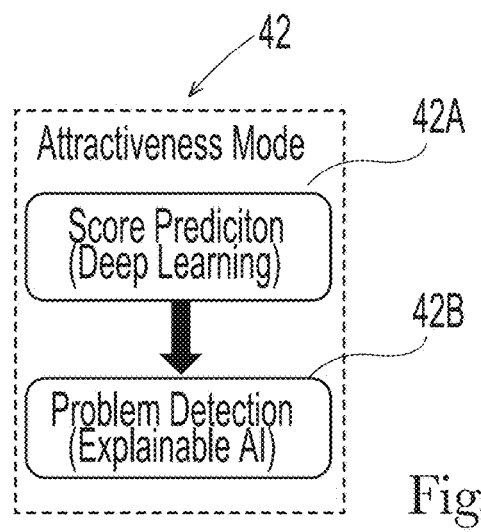
FIG. 3 is a diagram illustrating an exemplary functional block diagram associated with generating an image description according to the present invention.

FIG. 3 is a diagram illustrating an exemplary functional block diagram of an attractiveness model module 42 containing image analysis logic 144*b* for analyzing positive and negative attributes of the facial image portion 52 of the person depicted in the digital image 51, generating an Attractiveness Score 57 and an image description 53 according to the present invention. Specifically, the attractiveness model module 42 may comprise a first attractiveness sub-module 42A for generating an Attractiveness Score 57 indicative of a perceived attractiveness of the facial image portion 52, and a second attractiveness sub-module 42B for generating an image description 53.

Figure 4:
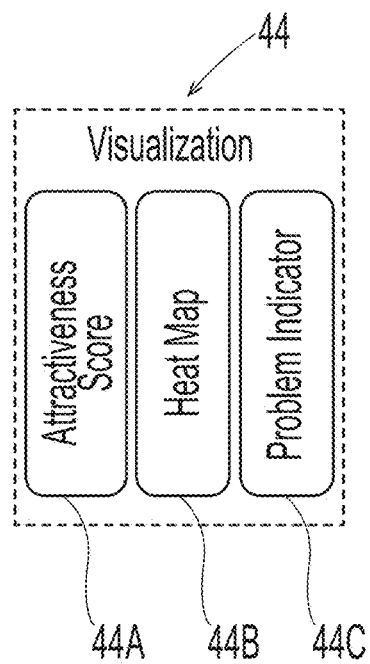
FIG. 4 is a diagram illustrating an exemplary functional block diagram associated with presenting an image description according to the present invention.

FIG. 4 is a diagram illustrating an exemplary functional block diagram of a visualization module 44 containing the GUI logic 144*c* for presenting an image description 53 according to the present invention. The visualization module 44 may comprise a first visualization sub-module 44A for presenting the Attractiveness Score 57, a second visualization sub-module 44B for presenting the image description 53 as a heat map, and a third visualization sub-module 44C for presenting the image description 53 as alternative text 531.

The facial image portion pre-processing module 40, the attractiveness model module 42 or the visualization module 44 may be implemented, in part or in whole, as software, hardware, or any combination thereof. In some cases, the attractiveness model module 42 may be implemented, in part or in whole, as software running on one or more computing devices or computing systems, such as on a server computing system or a client computing system. For example, the attractiveness model module 42 or at least a part thereof can be implemented as or within a mobile application (e.g. APP), a program or an applet, or the like, running on a client computing system such as the portable electronic device 12 of FIG. 1. The computing system may be in communication with a content server configured to store an obtained digital image or a plurality of obtained digital images. Each of the modules 40, 42, 44 can be implemented using one or more computing devices or systems that include one or more servers, such as network servers or cloud servers. Specifically, the processor 14*b* is configured to, based on the computer executable instructions, for implementing a method 200 for determining perceived attractiveness of a facial image portion of a person or persons in depicted in a digital image 51 according to the present invention as described herein after with respect to the flowchart of FIG. 5.

System and Method

Figure 5:
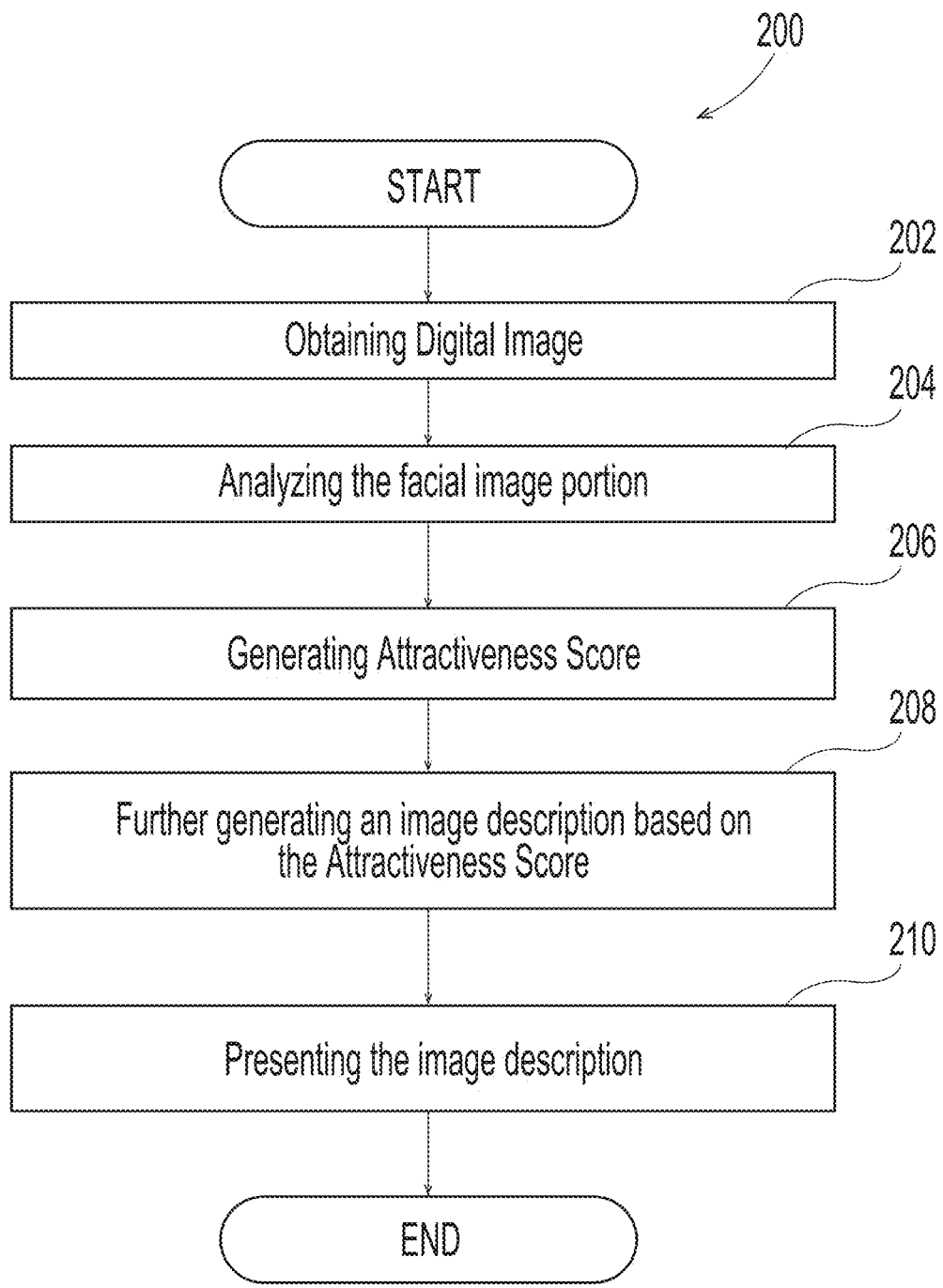
FIG. 5 is a flow chart illustrating a method for determining perceived attractiveness of a facial image portion according to the present invention.

Accordingly, the steps 202, 204, 206, 208, 210, 212, 214 of the method 200 according to the present invention is described hereinafter with reference to FIG. 5 as individual processes for performing each step. Each process may also be described as a sub-routine, i.e. a sequence of program instructions that performs a corresponding step according to the method 200 according to the present invention.

When the processor 14*b* is initiated, the processor 14*b* causes a first digital image 51 of at least a portion of a face of the subject to be obtained, e.g. via image obtaining logic 144*a* in step 202. The first digital image 51 may be a teeth image. The facial image portion 52 is a smile 521 defined by a combination of teeth and gum as shown in FIG. 6B, and the smile comprises positive and negative attributes. In step 204, the processor 14*b* analyzes the facial image portion 52 using a learning machine trained to evaluate the features of interest.

In step 206, an Attractiveness Score 57 is generated for the facial image portion 52.

The method 200 may comprise further generating an image description 53 comprising the facial image portion 52 in step 208 based on the Attractiveness Score 57, and presenting the image description 53 to a user for determining perceived attractiveness of the facial image portion 52 in step 210. Specifically, presenting the image description 53 may comprise one of: displaying the image description 53 in the digital image 51 as alternative text, displaying the image description 53 in the digital image 51 as a heat map, providing the image description 53 for audible presentation to the user, and combinations thereof.

By generating an Attractiveness Score 57 of a facial image portion depicted in a digital image provided by an user (consumer), further generating an image description 53 based on the Attractiveness Score and presenting the image description 53 to the consumer, users and/or consumers can obtain information related to the facial image portion 52 which impact perceived attractiveness of the facial image portion 52. It will be appreciated that the method 200 may also be adapted for application in image processing of other facial image portions such as for example, facial skin.

Human Machine User Interface

The present invention also relates to a human machine user interface (hereinafter "user interface") for determining perceived attractiveness of a facial image portion 52 in a digital image 51. The user interface may be a graphical user interface on a portable electronic apparatus including a touch screen display/display with an input device and an image obtaining device 18. The user interface may comprise a first area of the touch screen display displaying a first digital image of at least a portion of a face of the subject comprising a facial image portion obtained from the image obtaining device 18 and a second digital image interposed on the first digital image, the second digital image having the at least a portion of a face of the subject, the displayed facial image portion and the displayed image description for the displayed facial image portion. The user interface may further comprise a second area of the touch screen display different from the first area, the second area displaying a selectable icon for receiving a user input, wherein an image of at least one product recommendation item to improve perceived attractiveness of the facial image portion is displayed on the touch screen display if the user activates the selectable icon.

The method 200 for determining perceived attractiveness may be applied in various different applications including but limited to providing a product recommendation, providing personalized product use instructions to consumers, visualization of product efficacy, and to monitor progress in improvement in perceived attractiveness of a facial image portion after use of a recommended product. Although the following exemplary applications described hereinafter relate to oral features as a specific example of a facial image portion and such oral features include teeth, gum, and combinations thereof, it will be appreciated the method may be adapted for other facial features.

Figure 6A:
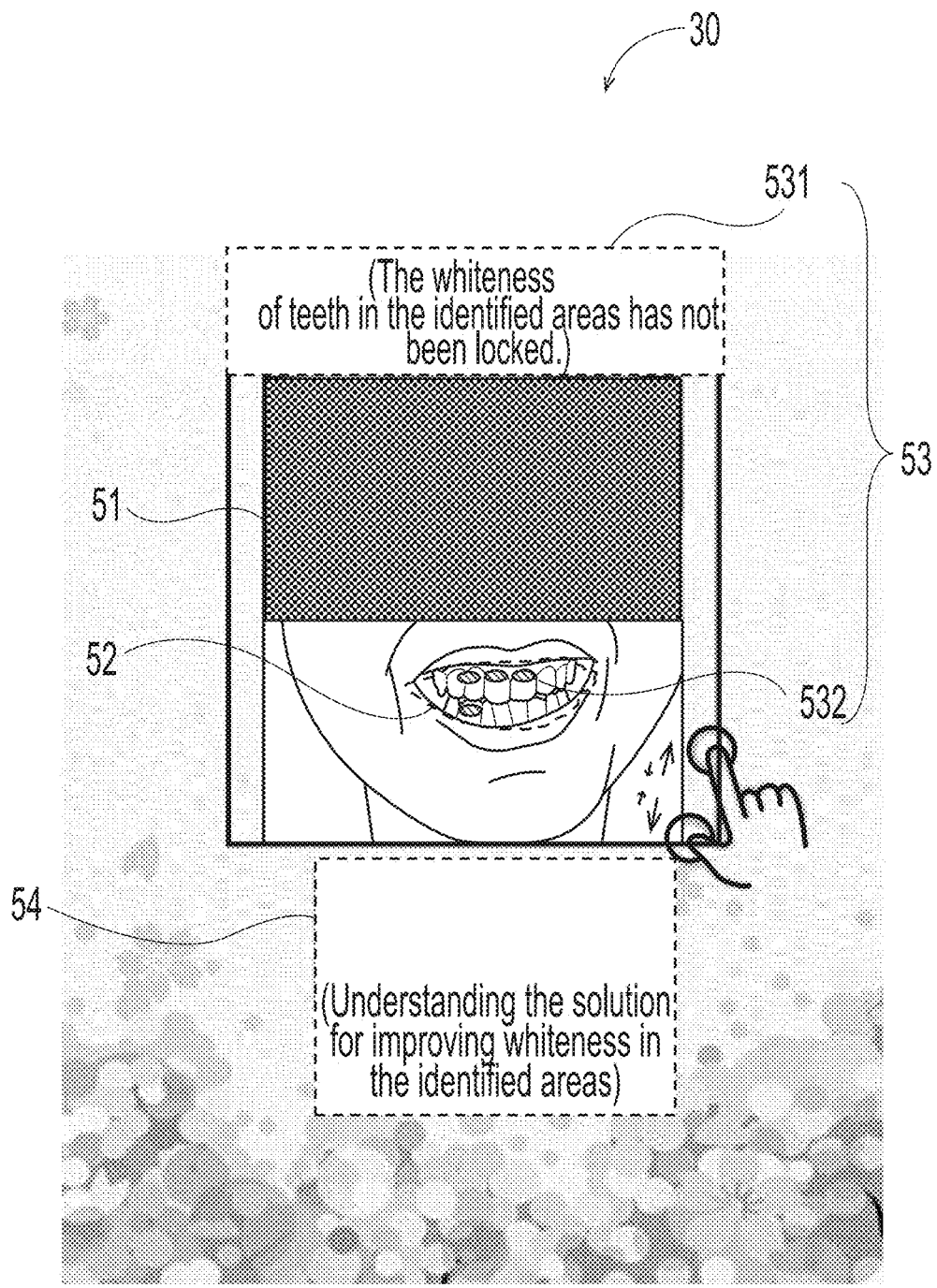
FIG. 6A is a screen shot illustrating an exemplary graphical user interface presenting a plurality of image descriptions to a user for visualizing perceived attractiveness of a smile in the digital image according to the present invention.
Figure 6B:
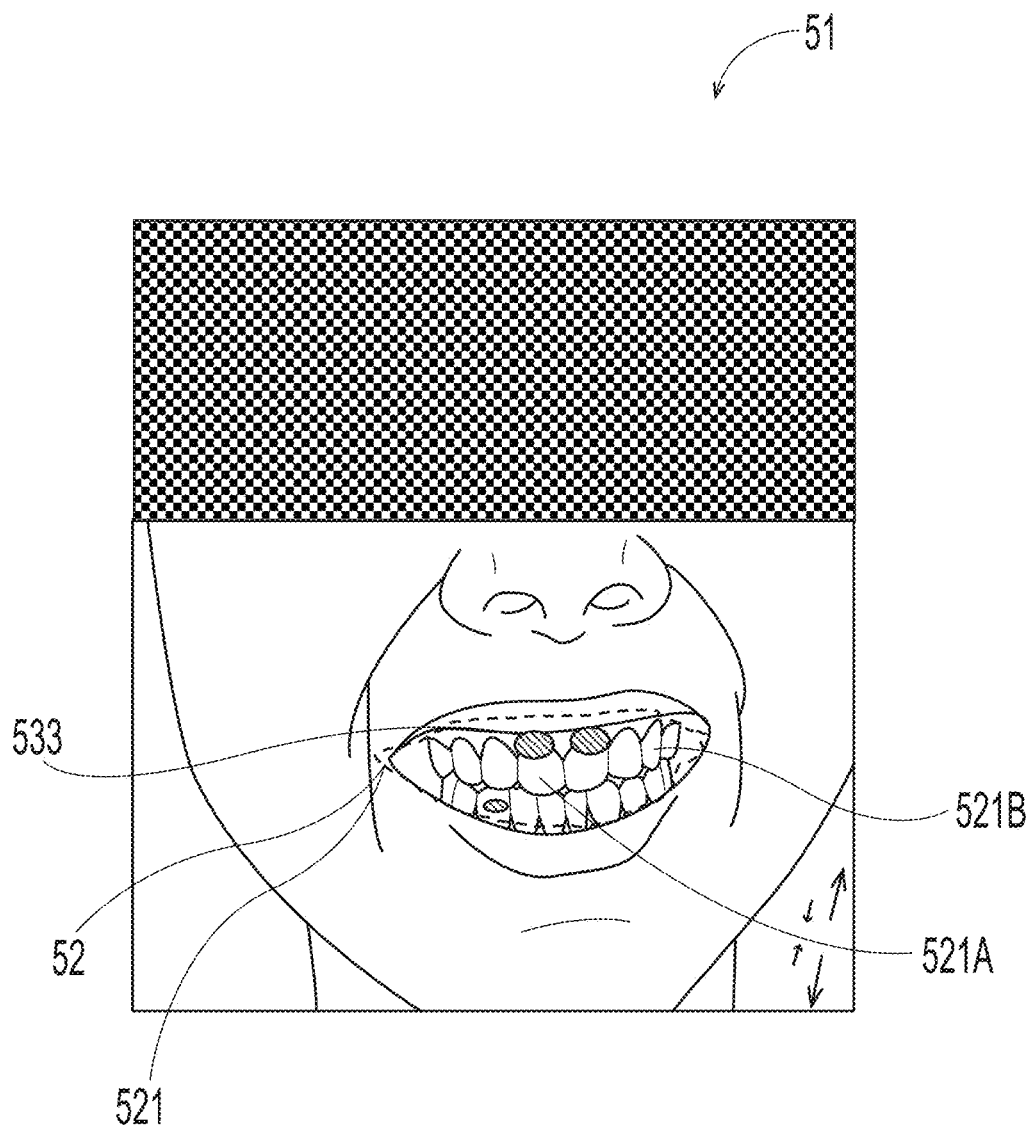
FIG. 6B is the digital image of FIG. 6A comprising an image description presented in the form of a heat map over the facial image portion depicted in the digital image according to the present invention.

FIG. 6A is a screen shot illustrating an exemplary graphical user interface 30 presenting an image description 53 of a facial image portion 52 of a person in the digital image 51 to a user for determining perceived attractiveness of the facial image portion 52 according to the present invention.

The digital image 51 may comprise a facial image portion 52 which the processor 14b has been programmed to determine perceived attractiveness for and there the facial image portion 52 is detected by the processor 14b (hereinafter "detected facial image portion 52") by the pre-processing module 40. The facial image portion 52 may include one or oral features, one or more facial expressions, or combinations thereof. Oral features may include mouth, teeth, gum or any feature in the oral cavity. Facial expressions may include a smile.

There is an image description 53 for the detected facial image portion 52, and a selectable input screen object 54 disposed in the graphical user interface 30.

The image description 53 may comprise alternative text 531 displayed in the graphical user interface 30, a heat map 532 displayed on the digital image 51 that identifies at least one area (hereinafter "identified area") in the facial image portion 52 comprising the negative attributes of the facial image portion 52, or a combination of the alternate text 531 and the heat map 532. Specifically, the alternative text 531 includes a description that indicates the impact of the identified area in the facial image portion 52 on the perceived attractiveness of the facial image portion 52. For example, the heat map 532 may display parts of the teeth with different defects which require different corresponding oral care treatments. For example, the heat map 532 may include one or more region of interest highlighted in the teeth image associated with the person depicted in the digital image 51.

The selectable input screen object 54 may comprise a text label comprising a description of the feature of the selectable input screen object 54. The selectable input screen object 54 may comprise a text label describing directions for processing a request for additional information about the facial image portion 52, for example, the text label may comprise a description related to proceeding to a different user interface directed to a method for providing a product recommendation for improving perceived attractiveness.

As shown in FIG. 6A, the whiteness of the identified areas on the teeth may be improved, and accordingly the description may be related to understanding a solution for improving whiteness of the identified areas on the teeth, and consequently improve a perceived attractiveness of the detected facial image portion 52.

FIG. 6B is the digital image 51 of FIG. 6A with the heat map 532. Referring to FIG. 6B, the detected facial image portion 52 is a smile 521 defined by a combination of oral features, teeth and gum. The smile 521 comprises positive and negative attributes as described hereinafter. Specifically, at least a portion of the smile 521 is defined by a first oral feature 521A and a second oral feature 521B.

The first oral feature 521A may be a first tooth and the second oral feature 521B may be a second tooth located in a different part of an area of the facial image portion 52. The first oral feature 521A comprises a highlighted region of interest 533 of the heat map 532 highlighted in the teeth image thereby indicative of negative oral attribute (yellowness). On the other hand, the second oral feature 521B does not comprise a highlighted region of interest of the heat map 532 highlighted in the teeth image thereby indicative of positive oral attribute (whiteness).

Figure 7:
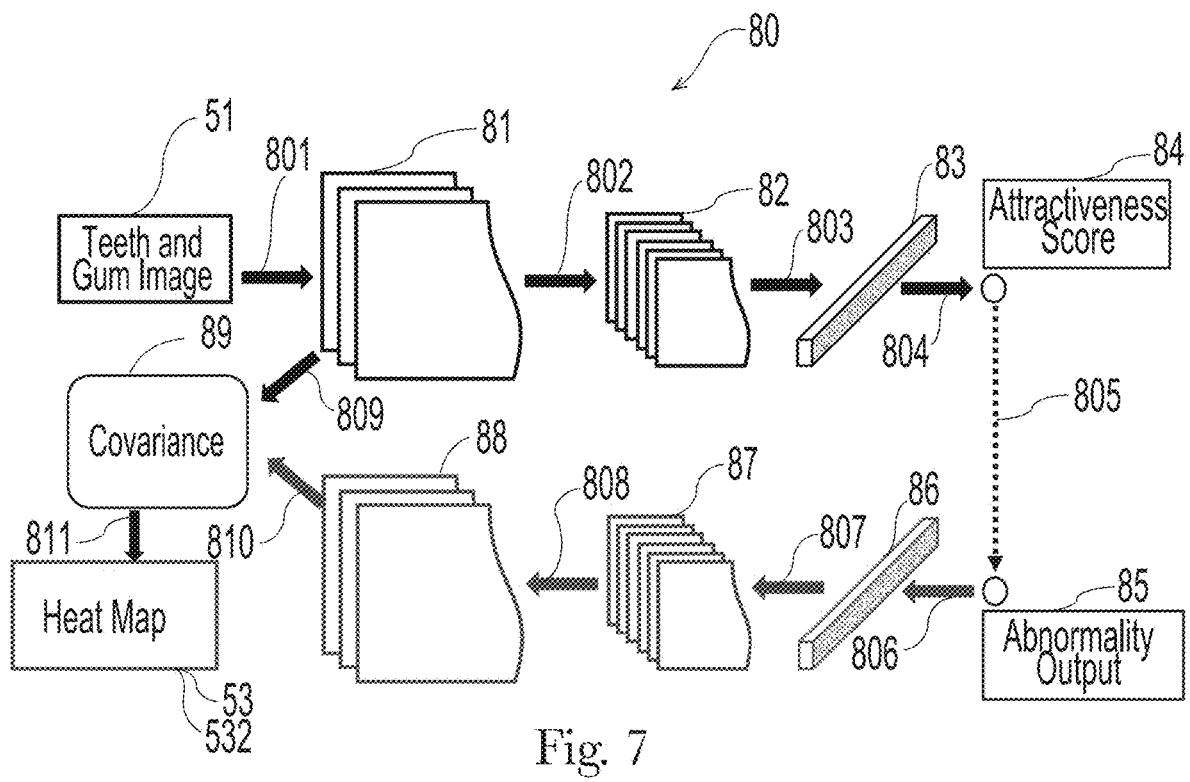
FIG. 7 is a schematic drawing illustrating the software architecture of a system according to present invention using an exemplary convolutional neural network (CNN) used for filtering the detected facial image portion and generating the image descriptor for determining perceived attractiveness of a facial image portion according to the present invention.
Figures 8A, 8B:
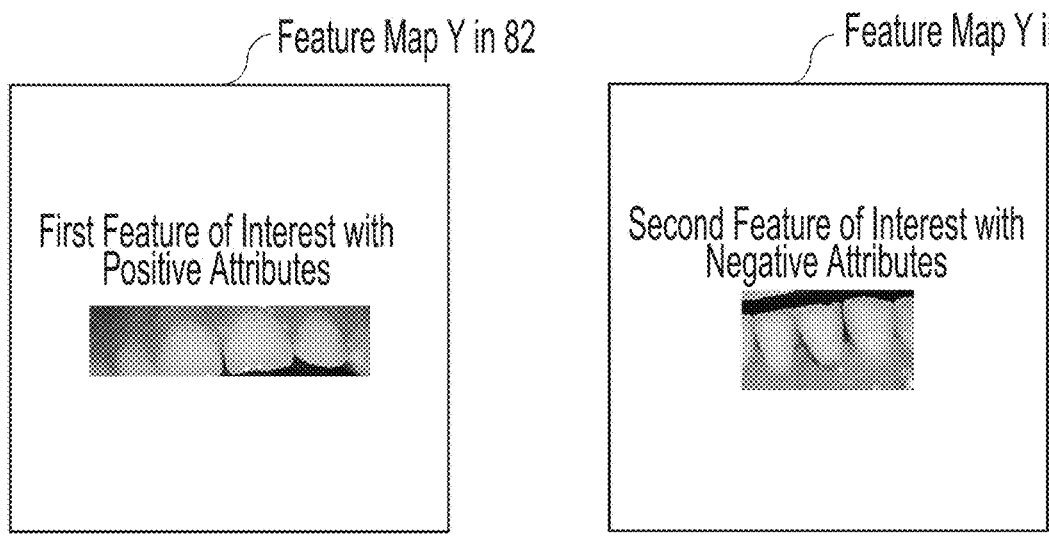
FIGS. 8A and 8B are conceptual illustrations of exemplary filter visualizations in a CNN of FIG. 10, showing features of interest depicted in one or more filtered feature maps according to the present invention.
Figures 9A, 9B, 9C:
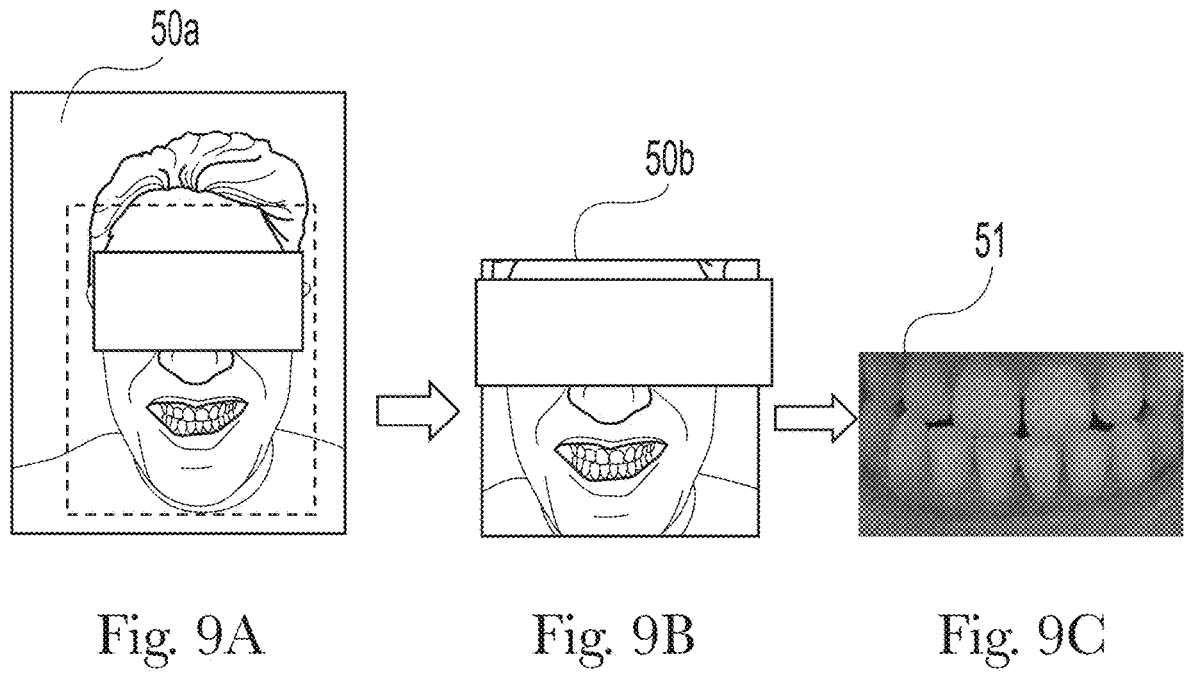
FIGS. 9A to 9C are a series of process flow diagrams illustrating a method of obtaining a digital image of a facial image portion according to the present invention.

FIG. 7 is a schematic drawing illustrating an exemplary system architecture 80 configured for implementing the method 200 based on a convolutional neural network (CNN) model. FIGS. 9A and 9B are conceptual illustrations of exemplary filter visualizations in the CNN model of FIG. 8, showing features of interest depicted in one or more filtered feature maps according to the present invention.

In the following description, the CNN model is described as an example of a machine learning algorithm, specifically a deep learning algorithm, for implementing methods and systems according to the present invention. Deep learning algorithms are concerned with building much larger and more complex neural networks and, as described hereinafter, the present invention is directed to analysis by a model trained by very large datasets of labelled analog data, such as digital images. Therefore, other deep learning algorithms which may be used to implement methods according to the present invention may include, but is not limited to, Recurrent Neural Networks (RNNs), Long Short-Term Memory Networks (LSTMs), Stacked Auto-Encoders, Deep Boltzmann Machine (DBM), Deep Belief Networks (DBN).

FIG. 7 illustrates the system architecture 80 of the CNN model, the CNN components which make up the CNN model, and exchanges between each CNN component for performing the method 200 according to the present invention. In general, CNN models are able to extract the hierarchies of visual features through stack-admissible neural layers equipped by receptive fields implementing convolutional kernels recognizing primary visual features to complex visual features of the image's components. In other words, each layer of the CNN model extracts rich information representing the original stimulus. Referring to FIG. 7, the system architecture 80 of the CNN model comprises CNN components which are operably connected through CNN exchanges arranged to generate the Attractiveness Score 57, the details of the CNN components and its respective function are described in Table 1 below.

TABLE 1

| Reference Number | CNN Component | Aspect of the Facial image portion in CNN component |
| --- | --- | --- |
| 81 | First Convolution layer having Feature Maps Kernel: 7 × 7 × 3 × 16 | Feature Maps with Positive Attributes |
| 82 | Second Convolution layer with Features Maps Kernel: 7 × 7 × 16 × 128 | Feature Maps with Positive Attributes |
| 83 | First set of Fully connected layers Feed Forward layers including 200, 100, and 50 hidden neurons. | Feature Maps with Positive Attributes |
| 84 | Attractiveness Score | Based on Positive Attributes and Negative Attributes |
| 85 | Abnormality Output | Negative Attributes |
| 86 | Second set of Fully connected layers Backward neural layers including 50, 100, 200 hidden neurons followed. | Negative Attributes |
| 87 | Third Convolution layer having Feature Maps. Dilated Transpose Convolution layer. Kernel: 128 × 16 × 7 × 7 | Negative Attributes |
| 88 | Fourth Convolution layer having Feature Maps. Dilated Transpose Convolution layer. Kernel: 16 × 3 × 7 × 7 | Negative Attributes |
| 89 | Covariance Operator | To highlight negative attributes in the presence of primary visual features. |

The actions performed in each CNN exchange connecting each of the above CNN components are described in Table 2 below, and the sequence of the analyzing step 204 and generating step 206 is according to the direction of CNN exchanges as shown in FIG. 7.

TABLE 2

| Reference Number | CNN Exchange Function | Action/information exchanged between CNN components |
| --- | --- | --- |
| 801 | Sampling | Sample one or more portions of the digital image to create one or more feature maps in a first layer 81 |
| 802 | Rectified Linear Unit | Non-linear function |
| 803 | Rectified Linear Unit | Non-linear function |
| 804 | Rectified Linear Unit | Non-linear function |
| 805 | Score loss operation | Unattractiveness score |
| 806 | Mirrored Rectified Linear Unit | Negative non-linear function |
| 807 | Mirrored Rectified Linear Unit | Negative non-linear function |
| 808 | Mirrored Rectified Linear Unit | Negative non-linear function |
| 809 | Rectified Linear Unit | Non-linear function |
| 810 | Mirrored Rectified Linear Unit | Negative non-linear function |
| 811 | 1 × 1 Convolution. Kernel: 3 × 1 × 1 × 1 | Feature maps to heat map conversion |

As shown in FIG. 7, analyzing may comprise filtering the digital image 51 in a first exchange 90 to obtain one or more filtered feature maps comprising features of interest associated with the facial image portion 52 and the features of interest are analysed. FIG. 8A shows a first filtered feature map X with positive attributes and FIG. 8B shows a second filtered feature map Y with negative attributes. Positive attributes may comprise whiteness of teeth, pinkness of gums, smoothness of teeth surfaces or positive appearances of the teeth or gums. Negative attributes may comprise teeth stains, gum redness, swollen gums or the like.

As shown in FIGS. 8A and FIG. 8B, the first and second features of interest are different. Specifically, referring to FIG. 7, and FIGS. 8A and 8B, the Attractiveness Score 57 may be generated based on a first set of characteristics associated with a first feature of interest in a first filtered feature map (Layer Y) and a second set of characteristics associated with a second feature of interest in a second filtered feature map (Layer Y). Referring to FIG. 8A, the first feature of interest may comprise a first plurality of oral features including gum and teeth located in an upper part of the oral cavity. Referring to FIG. 8B, the second feature of interest may comprise a second plurality of oral features including gum and teeth located in a lower part of the oral cavity.

The method may further comprise generating an abnormality output 85 indicative of the second feature of interest comprising negative attributes which negatively impact a condition of the first feature of interest.

Obtaining Digital Image

Figure 10:
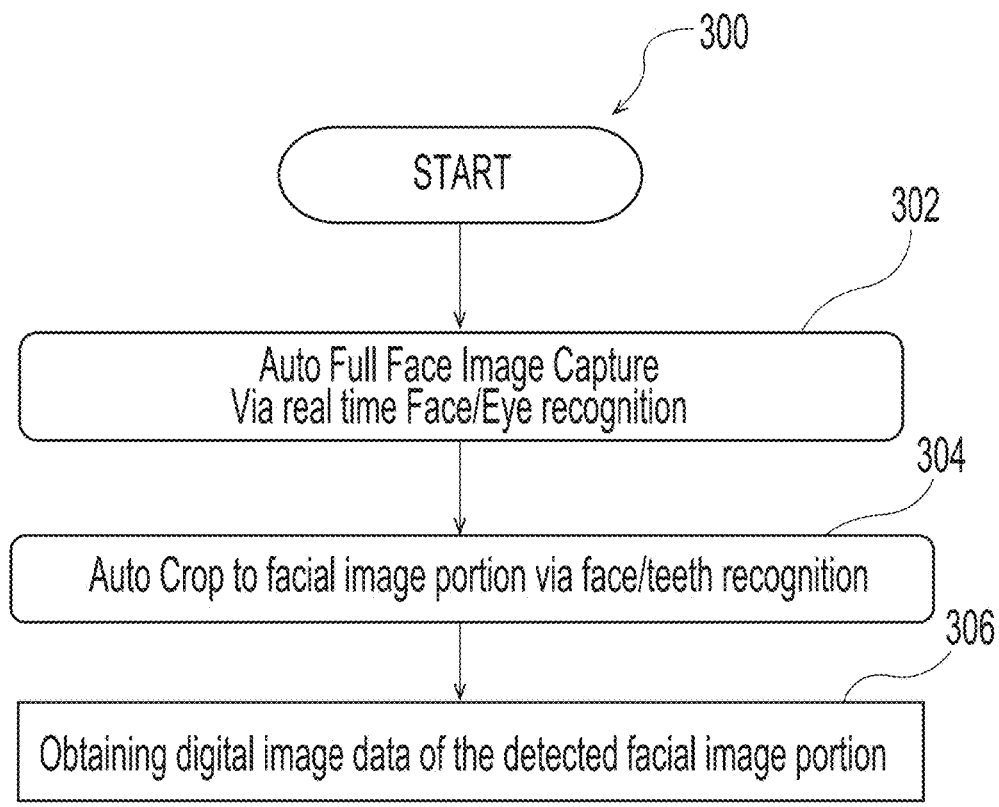
FIG. 10 is a flow chart illustrating a method of obtaining digital data image of a detected facial image portion according to the present invention.

The step 202 of obtaining a digital image according to the method 200 according to the present invention are described with reference to FIGS. 9A, 9B and 9C which is a series of process flow diagrams illustrating how the digital image 51 is obtained. FIG. 10 is a flow chart of a process 300 of obtaining the digital image 51 corresponding to the step 202.

An input image 50a of a face of a person is illustrated in FIG. 9A. The input image 50a may be taken by a user, for example, using the camera 18 of the portable electronic device 12. The input image 50a may also be further processed by machine learning and computer vision techniques to detect the person's face and/or facial image portion automatically. For example, the method 300 may comprise a face detection module that employs a Dlib face detection library to detect a face depicted in the input image 50a and draw a first detector box 55 bounding the detected face in the input image 50a. An example of how to apply a Dlib face detection library for finding facial landmarks for detecting faces in digital images may be found at the following published reference namely, D. E. King. *Dlib-ml: A machine learning toolkit*. J. Mach. Learning Research, 10:1755-1758, 2009.

FIG. 9B illustrates a step 302 of cropping the input image 50a using the detector box 55 of FIG. 9A to obtain an edited image 50b which comprises at least a portion of the face comprising the smile of the person as an example of a facial image portion 52 according to the present invention. The second pre-processing sub-module 40B may be a feature detection module configured to detect facial features such as teeth and/or gum which define the facial image portion 52 (smile) and draw a second detector box bounding the facial image portion 52. The edited image 50b may be further cropped using the second detector box to obtain a digital image 51 in step 306 and as shown in FIG. 9C.

Generating Image Description

Figures 11A, 11B, 11C:
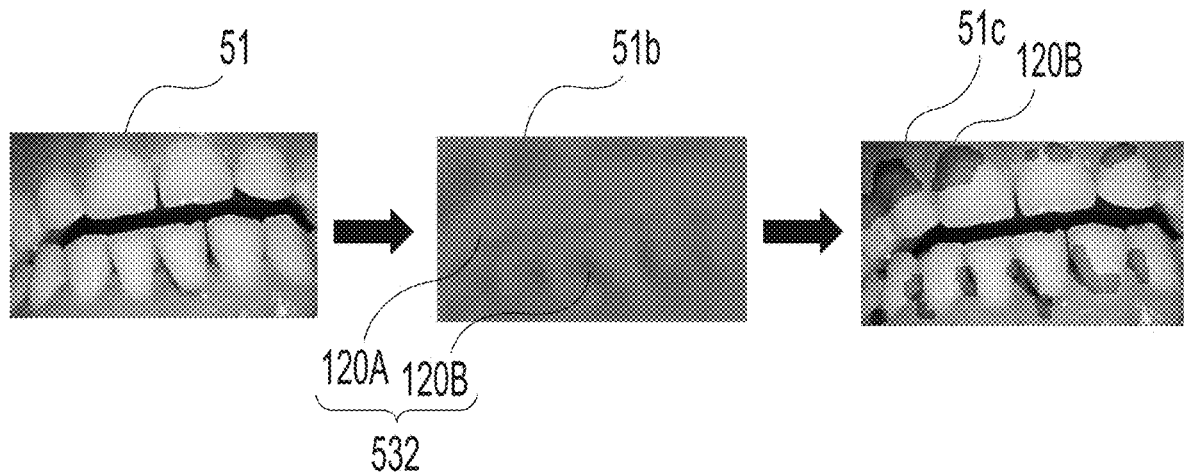
FIGS. 11A, 11B, and 11C are a series of process flow diagrams illustrating a method of generating an image description for a facial image portion according to the present invention.

Generating an image description 53 according to the present invention is described with respect to FIGS. 11A, FIG. 11B and FIG. 11C.

FIG. 11A illustrates a digital image 51 comprising a facial image portion 52 depicted in the digital image 51 before analysis. The digital image 51 may be cropped according to the method 300 of obtaining a digital image. FIG. 11B illustrates a second digital image 51b comprising an image description 53 presented visually as a heat map 532 overlaying the digital image 50.

Displaying the image description 53 in the digital image 51 as a heat map 532 may comprise generating the heat map 532, wherein generating the heat map comprises overlaying a layer 120B on at least a portion of the digital image 52 comprising the facial image portion, wherein the layer 120B is a pixel map that identifies the at least one area comprising at least one of said analyzed negative attributes.

Specifically, the heat map 532 visualizes the positive attributes as a second layer 120A and visualizes the negative attributes as the layer 120B in the at least one area in the facial image portion 52 depicted in the digital image 51. FIG. 11C illustrates a third digital image 51c comprising the facial image portion 52 having the heat map 532 with the layer 120B only overlaid on the facial image portion 52 to depict negative attributes present in the facial image portion 52 only. Although the above description relates to depiction of negative attributes present in the facial image portion 52 only, it will be appreciated that the heat map 532 may be configured to have the layer 120A only overlaid on the facial image portion 52 to depict positive attributes present in the facial image portion 52 as shown in the third digital image 51c.

Figures 12A, 12B:
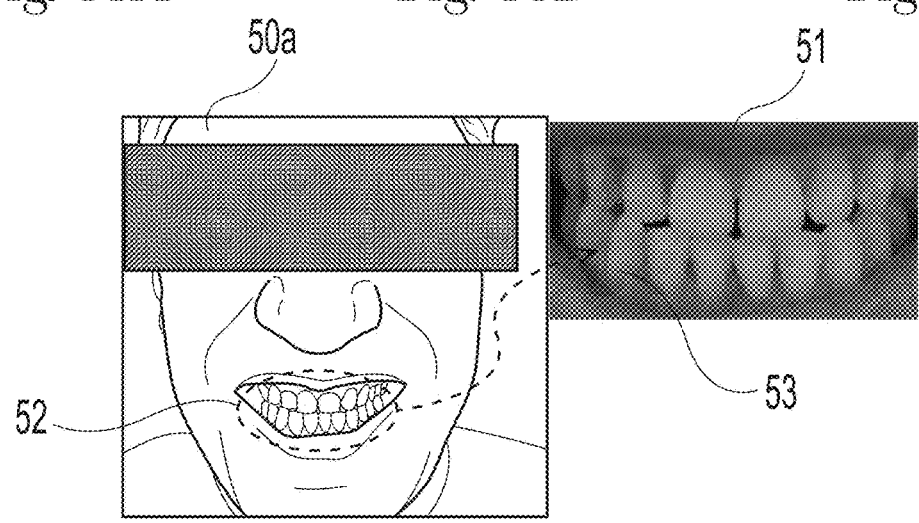
FIG. 12A illustrate a digital image illustrating an exemplary presentation of an image description for a facial image portion to a user according to the present invention.
FIG. 12B is a detailed view of the facial image portion depicted in the screen shot of FIG. 12A.
Figures 13A, 13B:
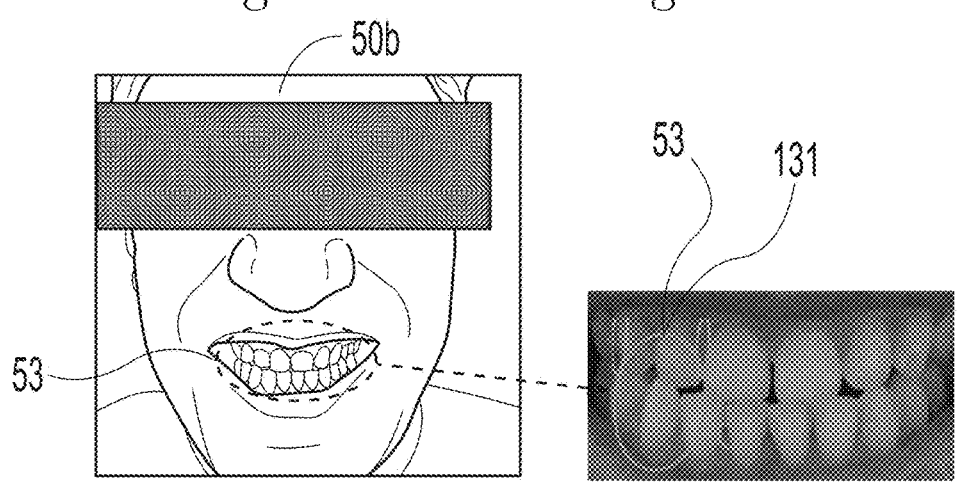
FIG. 13A illustrate a digital image illustrating a variation of an exemplary presentation of an image description for a facial image portion to a user according to the present invention.
FIG. 13B is a detailed view of the facial image portion depicted in the screen shot of FIG. 13A.

Referring to FIG. 12A, 12B, the image description 53 may be presented as a color region 130 on the teeth to indicate the areas for improving perceived attractiveness of the smile (facial image portion 52) of the person. Alternatively, referring to FIG. 13A, 13B, the image description may be presented in the form of colored boundary lines 131 that frame regions on the teeth to indicate the areas for improving perceived attractiveness of the smile of the person.

Product Recommendation

Figure 14:
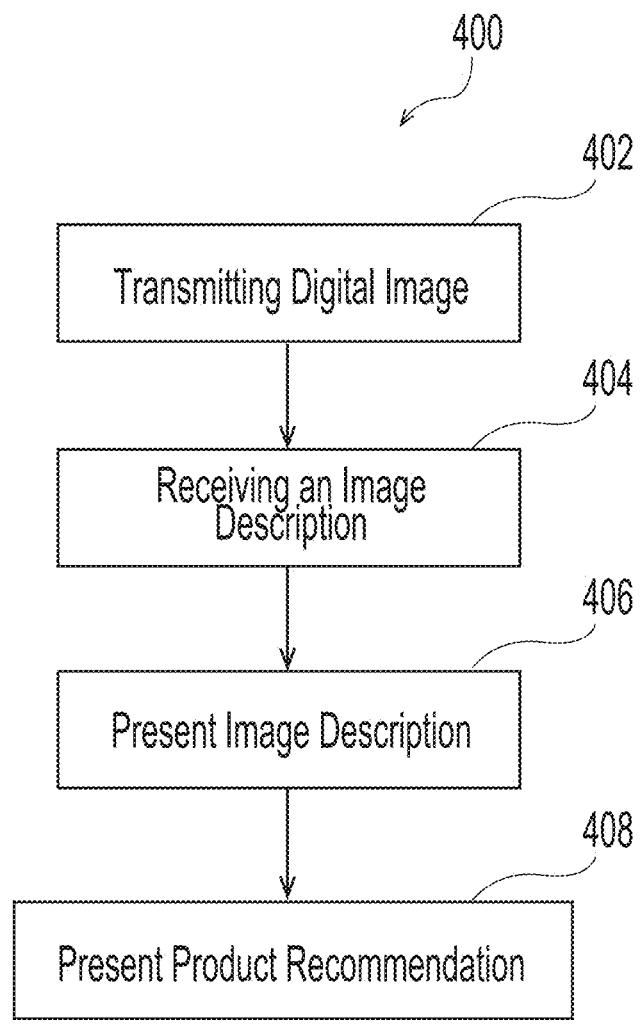
FIG. 14 is a flow chart illustrating a method of providing a product recommendation to improve perceived attractiveness of a facial image portion according to the present invention.

FIG. 14 is a flow chart illustrating a method 400 for providing a product recommendation for improving perceived attractiveness of a facial image portion 52 depicted in a digital image 51. FIGS. 15A to 15E are screen shots, each illustrating an exemplary user interface cooperating with each other for providing a product recommendation according to the present invention. Although FIGS. 15A to 15E are described as a series of user interfaces which are provided in a sequential manner in response to a preceding user interface, it will be appreciated that the user interfaces of FIGS. 15A to 15E may be programmed in multiple ways to define an overall user interface for providing a product recommendation according to methods according to the present invention as described hereinbefore. Preferably, all the user interfaces of FIGS. 15A to 15E define an exemplary user interface for providing a product recommendation for improving perceived attractiveness according to the present invention.

Referring to FIG. 14, the method comprises transmitting a digital image of at least one person in step 402, wherein the digital image comprises a facial image portion of the at least one person, wherein the facial image portion has both positive and negative attributes.

In step 404, an image description is received wherein the image description identifies at least one area in the facial image portion comprising at least one of the negative attributes analysed using the method 200. The image description is presented in step 406. In step 408, a product recommendation for improving perceived attractiveness of the at least one of the analyzed positive and/or negative attributes is presented to a user.

Figure 15A:
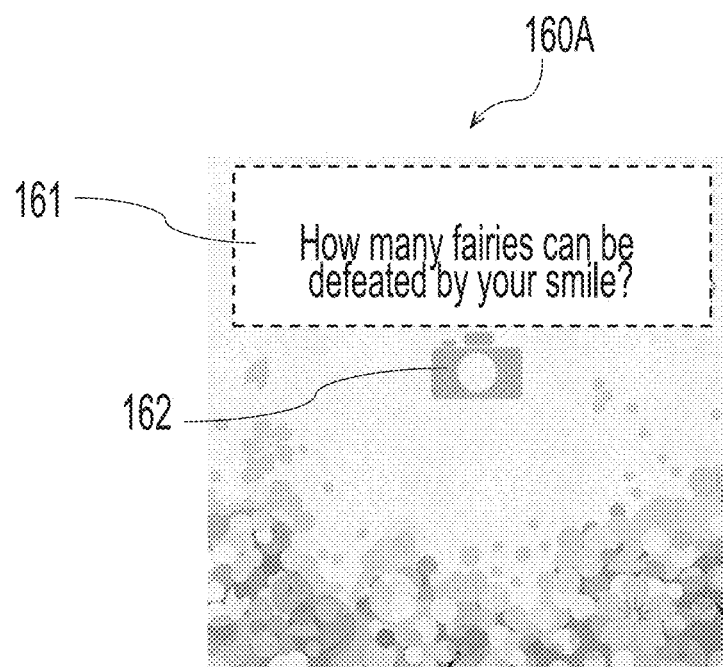
FIGS. 15A to 15D are screen shots, each illustrating an exemplary user interface for determining perceived attractiveness of a facial image portion according to the present invention.

FIG. 15A is a screen shot of a user interface 160A for transmitting an input image 50a of a face of a person to the apparatus 14 of FIG. 1 according to step 402. The user interface 160A may display a first text object 161 wherein the first text object 161 may comprise any terms and/or phrases that can be used to describe information about a method for determining perceived attractiveness of a facial image portion of a person according to the present invention. In an exemplary embodiment, the first text object 161 may include text depicted in the user interface 160A that relates to a method of comparing perceived attractiveness of a facial image portion 52 of a person relative to a population of people or a rhetorical question, i.e. "Do you have a winning smile?". Specifically, the first text object 161 may include an advertising device used in advertisements for engaging consumers, e.g. a question related to the facial image portion 52. The input image 50a may be captured by a user and transmitting the input image 50a to the apparatus 14, for example, using a mobile phone as a selfie image through a selectable icon 162 displayed on the user interface 160.

Figure 15B:
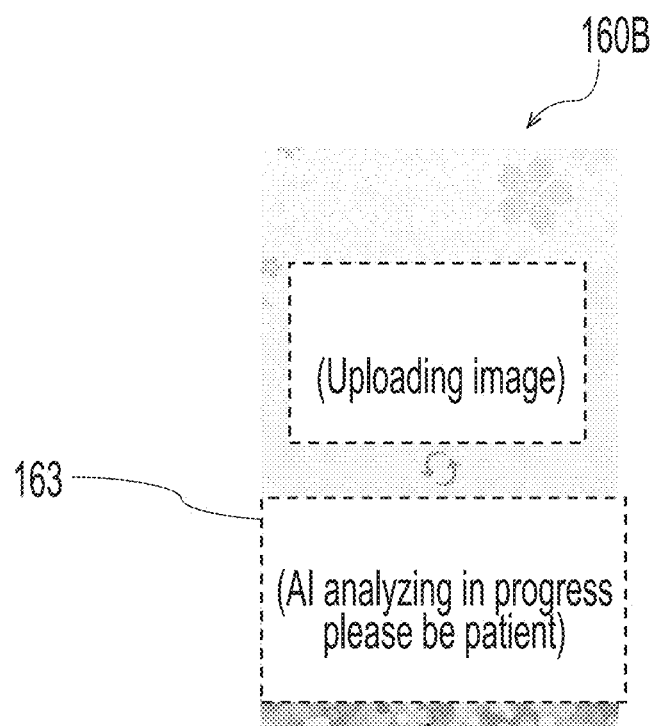
Figure 15C:
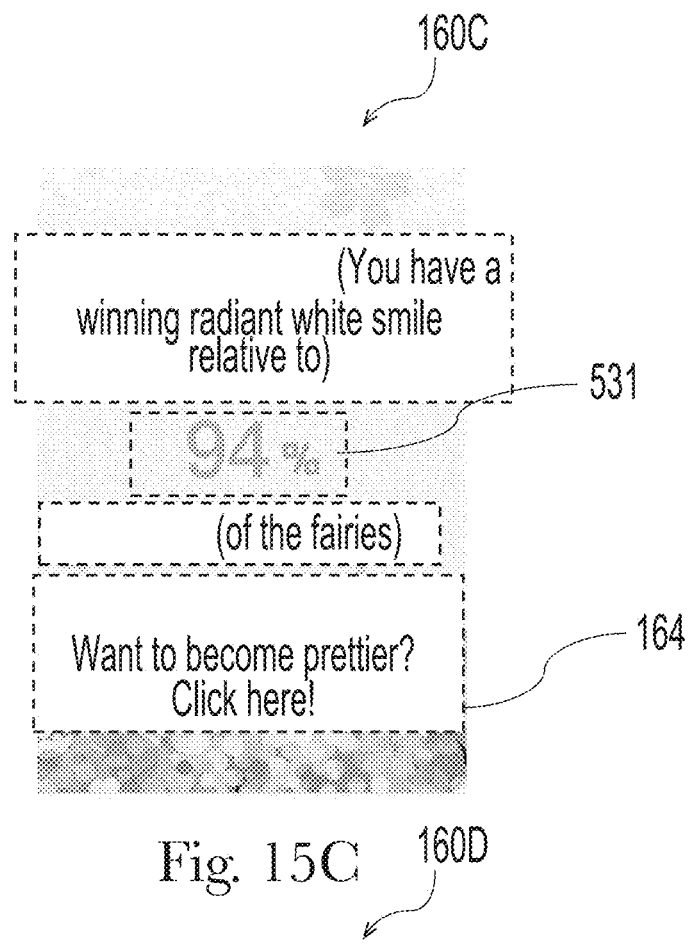

FIG. 15B is a screen shot of a user interface 160B that displays a second text object 163 to the user that indicates a status of the method 400. Referring to FIG. 15C, a user interface 160C displays alternative text 531 indicative of an Attractiveness Score 57 that is obtained in step 404. The image description 53 may further comprise alternative text 531a displayed in the user interface 160D wherein the alternative text 531a is associated with information about the Attractiveness Score. The alternate text 531a may be an Attractiveness Aggregate, such as for example an aggregate value calculated according to a mathematical formula based on the Attractiveness Score.

Figure 15D:
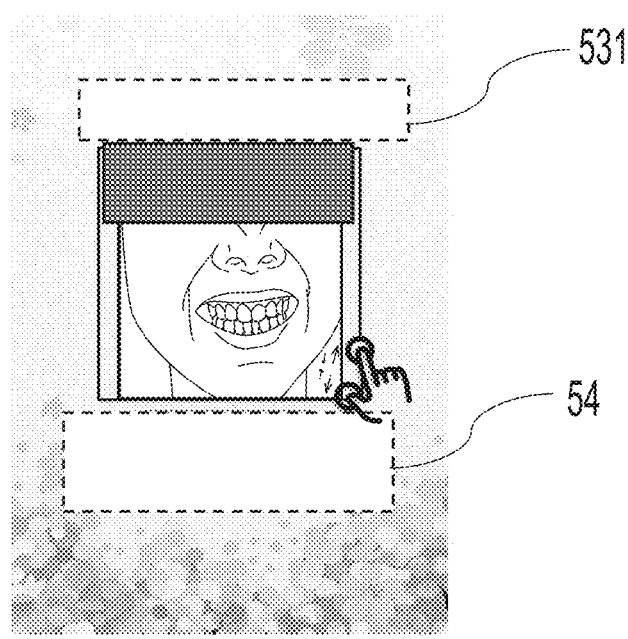

The user interface 160C further displays a selectable input icon 164 for sending a request to present the image description 53 in the form of a heat map 532 in step 406 as shown in FIG. 15D. Referring to FIG. 15D, a user interface 160D is similar to the user interface 30 of FIG. 6A and shown to illustrate a sequence of the series of user interfaces that form part of the method described hereinbefore.

Figure 15E:
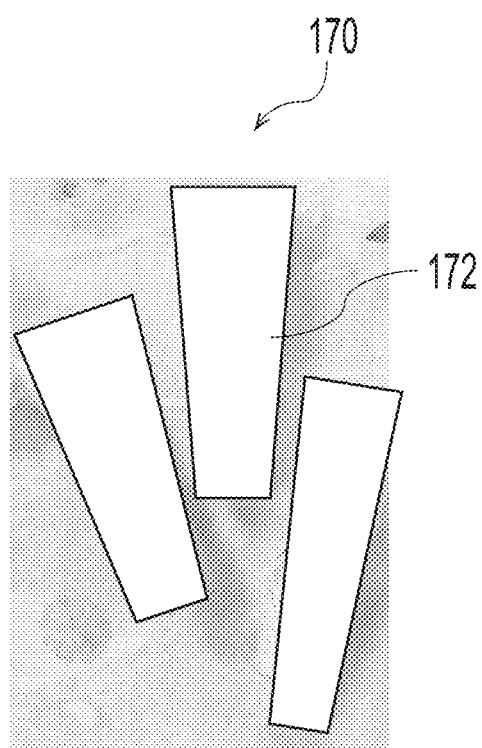
FIG. 15E is a screen shot, illustrating an exemplary user interface for displaying details of a product recommendation for treating facial features defining a facial image portion so as to improve perceived attractiveness of the facial image portion.

The facial image portion 52 that is being determined is the smile of a person depicted in the digital image 51 and accordingly the product recommendation shown in a user interface 170 of FIG. 15E is an oral care product 172 for improving perceived attractiveness of the smile.

The image description 53 may comprise alternative text 531 related to oral care information described hereinafter:
1) Brush more carefully and/pay more attention to the region of interest indicated in the heat map ("region of interest")
2) The whitening is not optimized in the region of interest
3) The regions of interest are not white enough
4) The regions of interest are corners in the mouth which are hard to access with the toothbrush during brushing (hereinafter "brushing dead corners")
5) The regions of interest are brushing dead corners that need to be brushed more carefully.

Visualization of Efficacy of Customized Oral Care Regimen

Figure 16:
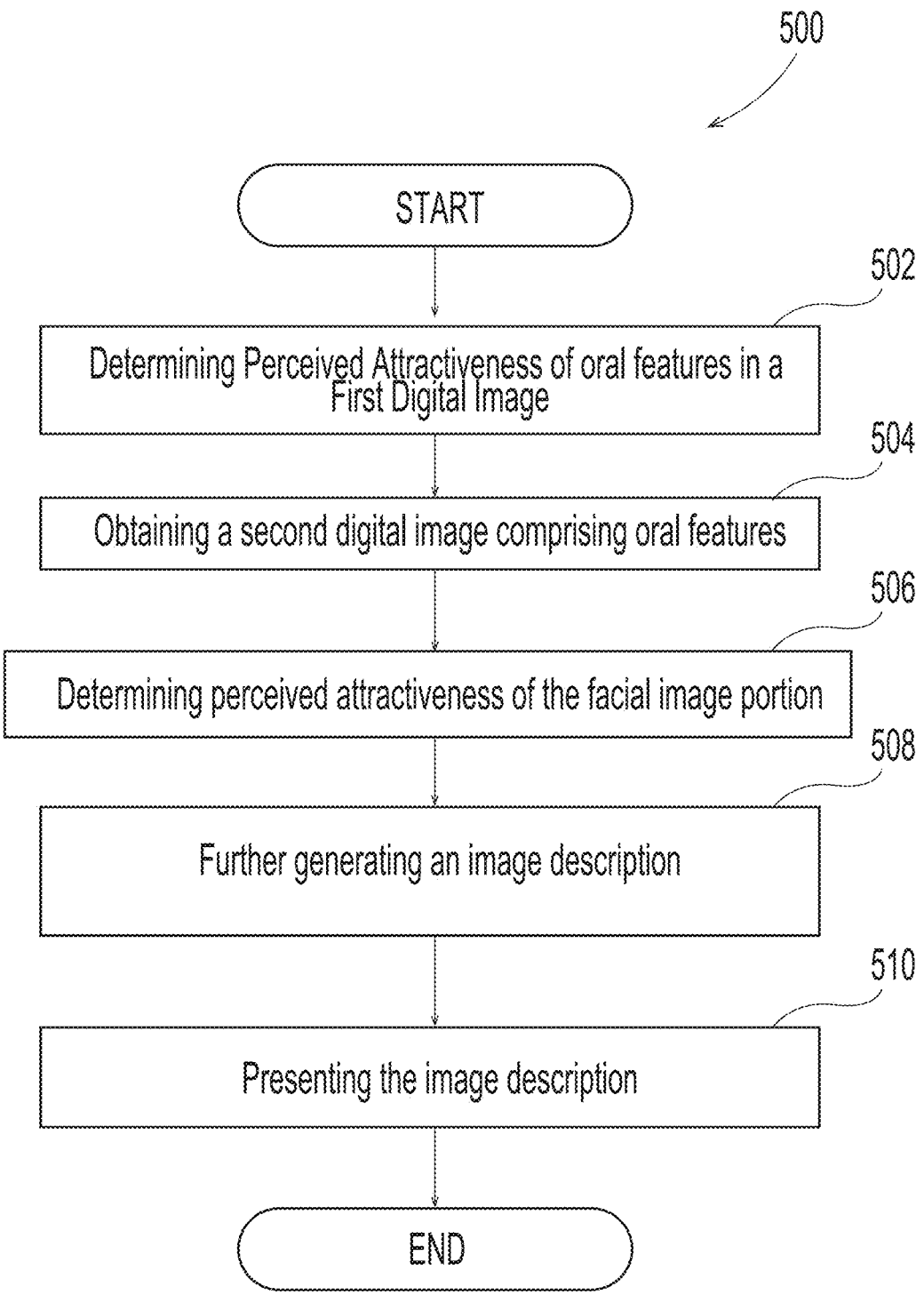
FIG. 16 is a flow chart illustrating a method of demonstrating efficacy of a customized oral care regimen in improving perceived attractiveness of one or more oral features of at least one person depicted in a digital image according to the present invention.

The present invention also relates to a method of demonstrating efficacy of a customized oral care regimen to a user, and this method may be used by dental professionals for performing remote oral care consultation for users in need of treatment but who are not able to travel to the dental clinics at which the dental professionals are located. FIG. 16 is a flow chart illustrating a method 500 of demonstrating efficacy of a customized oral care regimen in improving perceived attractiveness of one or more oral features of at least one person depicted in a digital image according to the present invention. The customized oral care regimen may comprise providing brushing instructions and/or providing an oral care product recommendation to be used in conjunction with the brushing instructions. The method 500 may be used to analyze weekly images of one or more oral features (e.g. teeth and/or gums) to visualize stain areas on the teeth.

It is often a challenge to translate clinically measured efficacy of an oral care regime into consumer-relevant benefits because of the professional specificity of the clinical methods and as such consumers find it difficult to compare/remember the "before and after" status. Therefore, it is important to visualize progress of an oral care regimen and/or an oral care product efficacy through a method that provides an image description explains the "before and after" status of the oral features and make the image "talkable" and sharable.

Figure 17A:
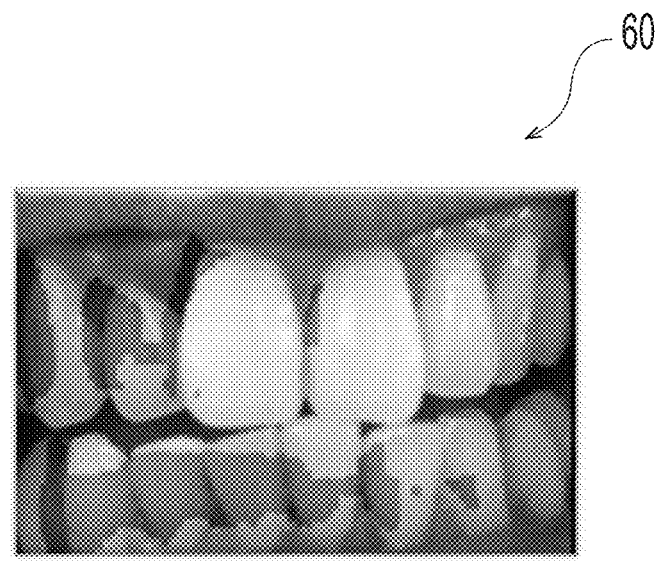
FIGS. 17A and 17B is a series of process flow diagrams illustrating the method of FIG. 16.

According to method 500, users may receive a personalized oral care consultation with product usage instructions at the supervised brushing and a picture of their teeth analyzed according to the method. Use of the method 500 may comprise several key benefits:

- The first digital image 60 shows areas to pay attention to—stained areas are labeled in bright pink (as shown in FIG. 17A).
- It is more convenient for dental professionals to provide oral care such as brushing instructions.
- It is easy for users to use at home.

The method 500 may comprise the steps of:
a) determining 502 perceived attractiveness of a facial image portion of a person in a first digital image 60, prior to treatment with a customized oral care regimen or an oral care product (see FIG. 17A);
b) obtaining 504 a second digital image 61 of the facial image portion of the person depicted in the first digital image, wherein the second digital image comprises the facial image portion of the person, wherein the facial image portion in the second digital image is treated with the customized oral care regimen or the oral care product for a predetermined time period;
c) determining 506 perceived attractiveness of the facial image portion in the second digital image 61 (see FIG. 17B);
d) comparing perceived attractiveness of the facial image portion in the second digital image 61 with perceived attractiveness of the facial image portion in the first digital image 60.

Figure 17B:
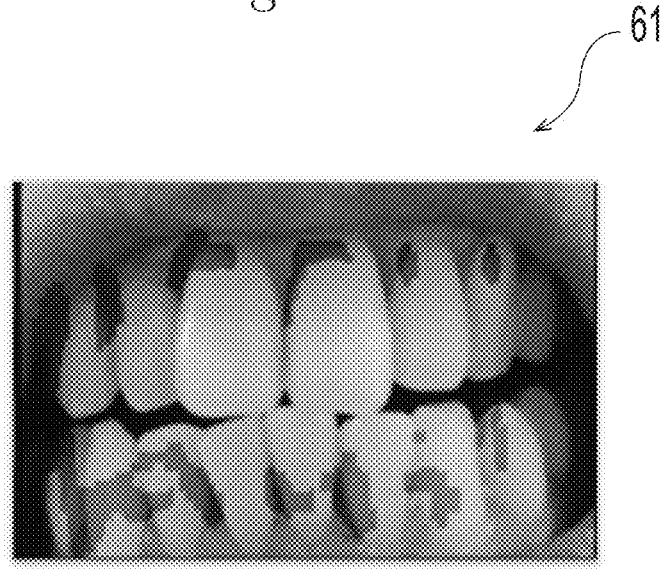

Specifically, FIG. 17A is a first digital image 60 of oral features of a subject determined for perceived attractiveness at Day 0, i.e. the start of a predetermined time period. FIG. 17B is a second digital image of oral features of the subject determined for perceived attractiveness at the end of the predetermined time period. The predetermined time period may be two weeks of use of a consumer product, such as an oral care product. The image descriptions in the first and second digital images identify at least one area in the oral features depicted in the digital images which comprise the analyzed negative attributes. Accordingly, to determine if there is a reduction in negative attributes of the oral features, the image descriptions may be analyzed for the pixel count to demonstrate if there has been a reduction in negative attributes. As shown in FIG. 17A, the image description for the oral care features in the first digital image 60 has 12714 pixels while the image description for the oral care features in the second digital image 61 of FIG. 17B has 7894 pixels. The reduction in the number of pixels correspond to a reduction in negative attributes of the oral care features. The negative attributes may be teeth stains. The facial image portion in the first digital image 60 may be treated with a reference product for comparative analysis between products.

Figure 18:
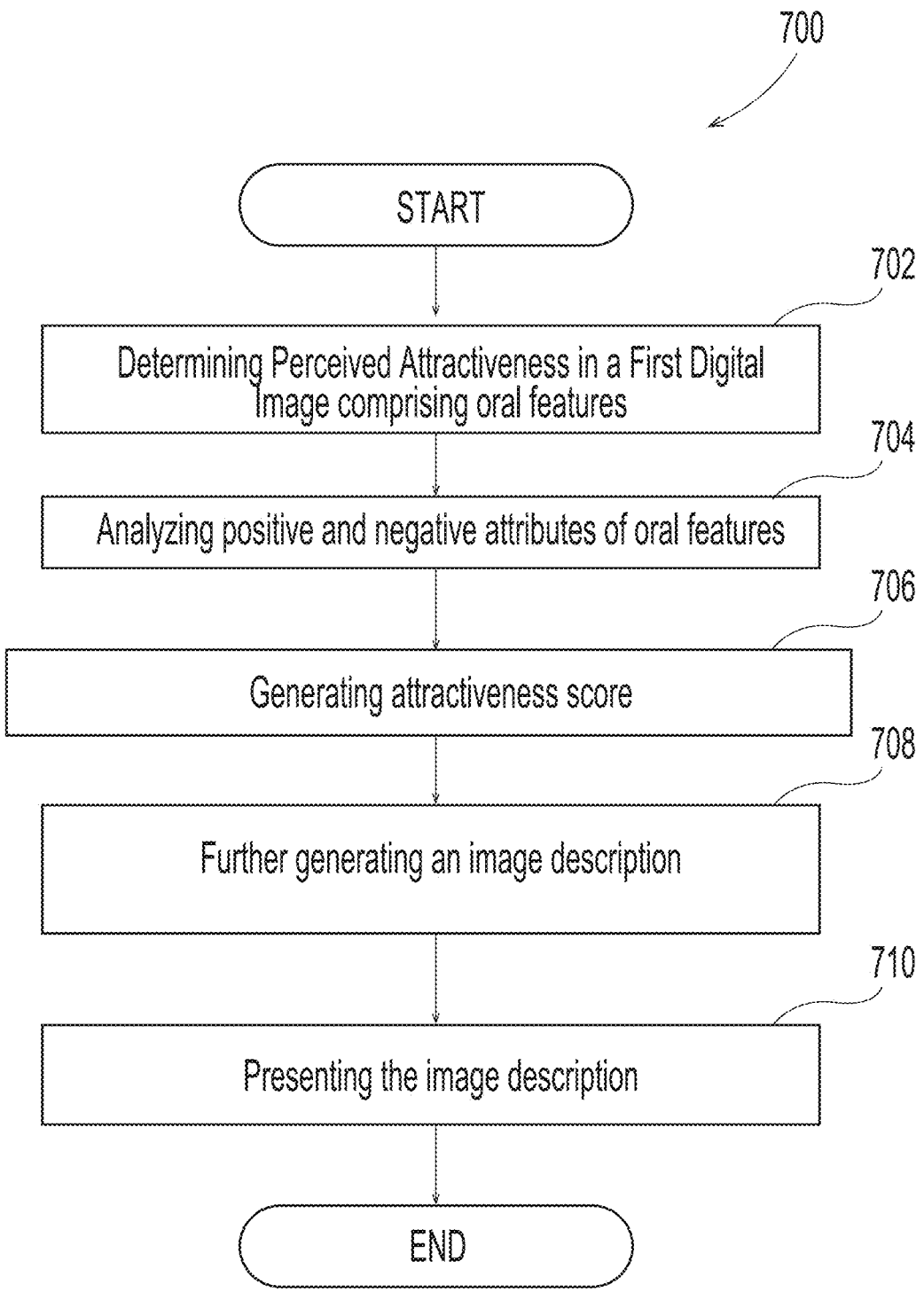
FIG. 18 is a flow chart illustrating a method of demonstrating efficacy of an oral care product according to the present invention.

FIG. 18 is a flow chart illustrating a method 700 of demonstrating efficacy of a consumer product or an oral care regimen over a product usage time period.

The method 700 may comprise the steps of:
i) determining perceived attractiveness of a facial image portion of a person in a first digital image, prior to treating the facial image portion with customized oral care instructions;
ii) obtaining a second digital image of the person depicted in the first digital image, wherein the second digital image comprises the facial image portion of the person, wherein the facial image portion in the second digital image is treated with a consumer product for a predetermined time period;
iii) determining perceived attractiveness of the facial image portion in the second digital image;
iv) comparing perceived attractiveness of the facial image portion in the second digital image with perceived attractiveness of the facial image portion in the first digital image.

Figure 19A:
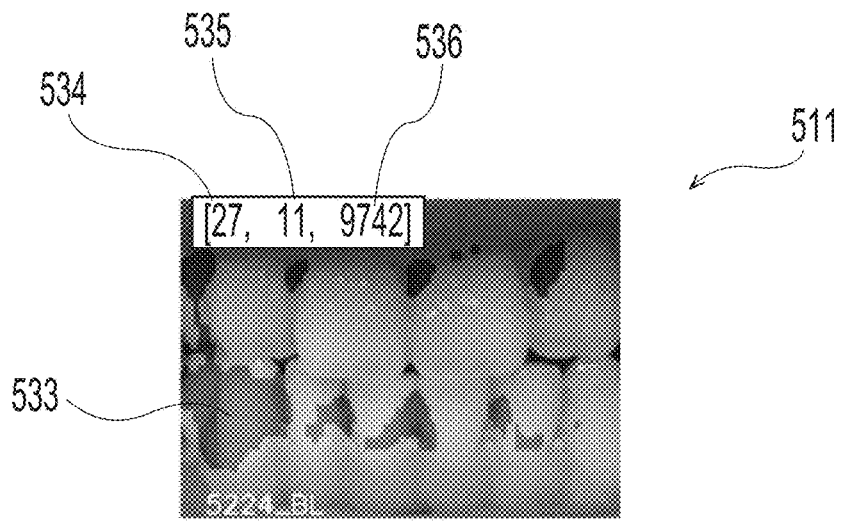
FIG. 19A is a digital image illustrating at least a portion of a facial image portion of a person at the start of a predetermined time period prior to treatment with a product recommendation, wherein perceived attractiveness of the facial image portion of the person is determined according to a method according to the present invention.

FIG. 19A is a first digital image 511 comprising at least a portion of a facial image portion 52 of a person. The digital image 511 is analyzed according to a method 200 according to the present invention at the start of a predetermined time period prior to performing the customized oral care instructions. The digital image 511 further comprises an image description that identifies a plurality of areas 533 in the facial image portion 52 comprising at least one analyzed negative attribute. Specifically, the image description is presented as a heat map 533. An Attractiveness Score 534 corresponding to a numerical value (for example 27), a first numerical value 535 corresponding to a number of identified areas (for example 11 identified areas), and a second numerical value 536 corresponding to a total number of pixels defining the identified areas (for example, 9742 pixels) are presented in the digital image 511 to provide information related to the perceived attractiveness of the facial image portion 52 to the user.

Figure 19B:
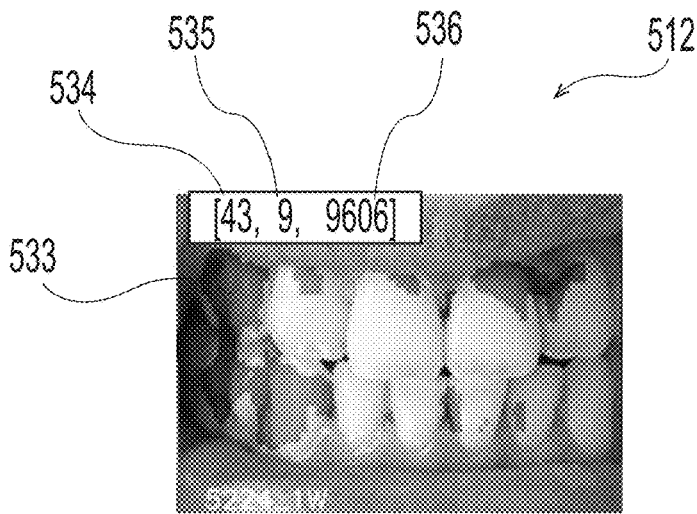
FIG. 19B is a digital image illustrating the at least a portion of a facial image portion of the person after 1 week of use of the product recommendation.
Figure 19C:
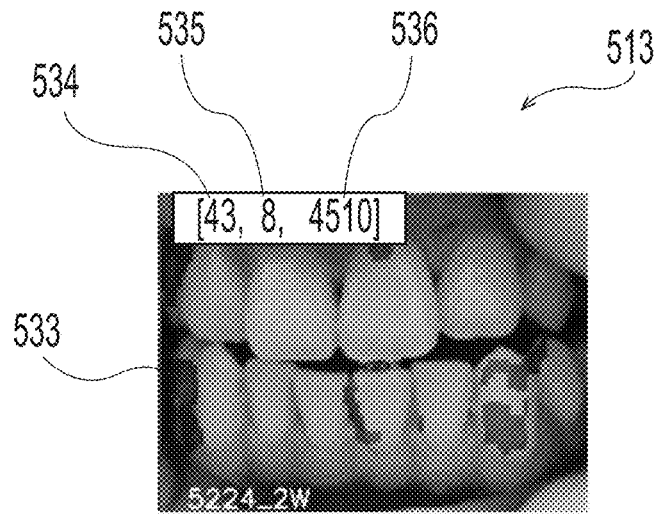
FIG. 19C is a digital image illustrating the at least a portion of the facial image portion of the person after 2 weeks of use of the product recommendation.

FIG. 19B is a second digital image 512 illustrating the at least a portion of a facial image portion of the person after 1 week of use of the product recommendation item. FIG. 19C is a third digital image 513 illustrating the at least a portion of the facial image portion of the person after 2 weeks of use of the product recommendation item. A summary of the improvement in the Attractiveness Score in FIG. 19B, FIG. 19C relative to FIG. 19A is described in Table 3 below.

TABLE 3

|  | Digital Image 511 (Control) | Digital Image 512 | Digital Image 513 |
| --- | --- | --- | --- |
| Attractiveness Score 534 | 27 | 43 | 43 |
| First Numerical Value 535 corresponding to a Number of Identified Areas 533 | 11 | 9 | 8 |
| Second Numerical Value 536 corresponding to total number of pixels in the number of identified areas | 9742 | 9606 | 4510 |

Specifically, the reduction in the number of identified areas corresponding to negative attributes of the oral features demonstrate that use of the product recommendation reduces the negative attributes thereby improving the Attractiveness Score, and consequently a perceived attractiveness of the facial image portion.

The method may comprise a step of repeating the determining step and comparing in step (iv) over a predetermined period of time. The predetermined period of time may be one week, preferably two weeks, more preferably three weeks. A technical effect is that it enables tracking of an improvement in the perceived attractiveness of the facial image portion over the predetermined period of time thereby allowing users to monitor progress and product usage accordingly. The perceived attractiveness of the facial image portion may include one or more oral features of at least one person depicted in a digital image. The one or more oral features may include but is not limited to, teeth, and the perceived attractiveness is teeth whitening.

Method of Tracking Improvement in Perceived Attractiveness

Figure 20:
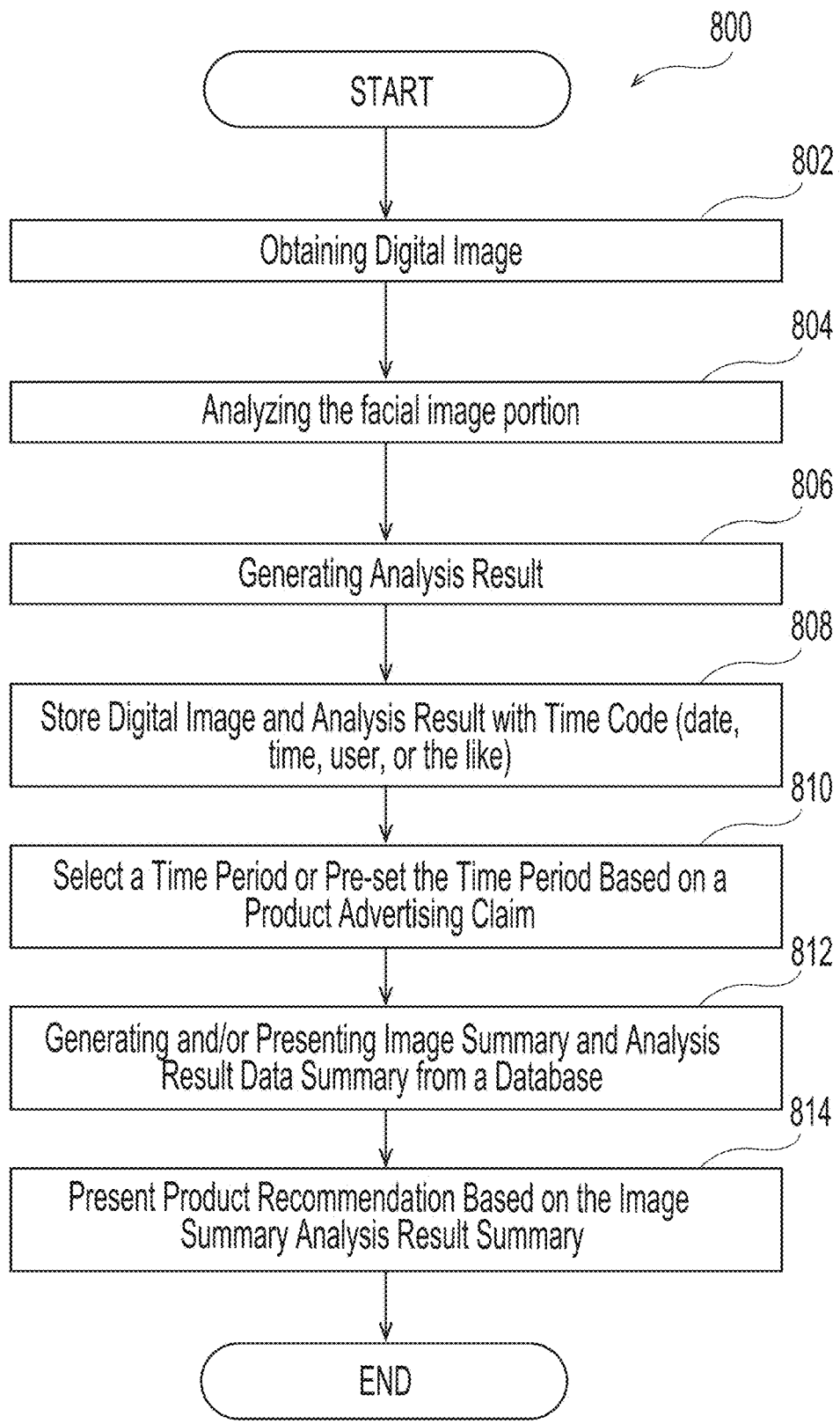
FIG. 20 is a flow chart illustrating a method of tracking improvement in the perceived attractiveness of the facial image portion of one or more oral features of at least one person depicted in a digital image according to the present invention.

FIG. 20 is a flow chart illustrating a method 800 of tracking improvement in perceived attractiveness of the facial image portion of one or more oral features of at least one person depicted in a digital image according to the present invention. For example, the oral feature may be teeth and the method 800 may be used to keep recording and tracking of a digital image of a person's teeth and an analysis result so that the method could repeat the analysis based on the timing to show improvement/progress of their teeth attributes (e.g. teeth whitening) and/or attractiveness during a period of time. This function could be used to support product advertising claims including but not limited to "21 days teeth whitening challenge", "whiten your teeth in a predetermined number of days", "whitening longevity (锁白)", "long lasting (24 h) whitening", or any teeth whitening related attributes.

The product may be an oral care product including but limited to toothpaste, white strip, mouth rinse or any form suitable for applying an oral care treatment. Although teeth attractiveness is described as a desired attribute related to perceived attractiveness in the method 800, it will be appreciated that the method 800 can be applied to other attributes including but not limited to healthy gums, teeth shine, or any other consumer relevant descriptions that may be used for the image description relative to oral feature attributes as described hereinafter in Table 5.

The method 800 may comprise the following steps of:
obtaining 802 a digital image of at least a portion of a face of the subject to be obtained, e.g. via image obtaining logic 144a. The digital image 51 may be a teeth image.
analyzing 804 the facial image portion 52 using a learning machine trained to evaluate the features of interest.
generating 806 an analysis result for the facial image portion 52.
Storing 808 the digital image and the analysis result with time code that identifies the digital image with the analysis result. The time code may include but is not limited to date, time, user information or the like.
selecting 810 a time period or preset the time period based on a product advertising claim.
Generating 812 an image description based on the analysis result in step 806. Optionally, the image description may be presented in step 812.
Optionally, further presenting 814 a product recommendation.

The analysis result in step 806 may comprise an attractiveness score, at least one area of the one or more oral features that consumers still need to improve, or other data generated by the Attractiveness model described hereinbefore.

Specifically, generating the image description in step 812 may comprise generating an image summary and an analysis result data summary from the analysis results from a database. The database may be stored on a server coupled to the system. Optionally, the method 800 may comprise further presenting in step 814 a product recommendation including but not limited to, continued usage of a product (currently used by the consumer) for a predetermined number of days, adding a new product to the consumer's oral care regimen for a better result, or any suitable treatment for improving teeth attractiveness.

Figure 21:
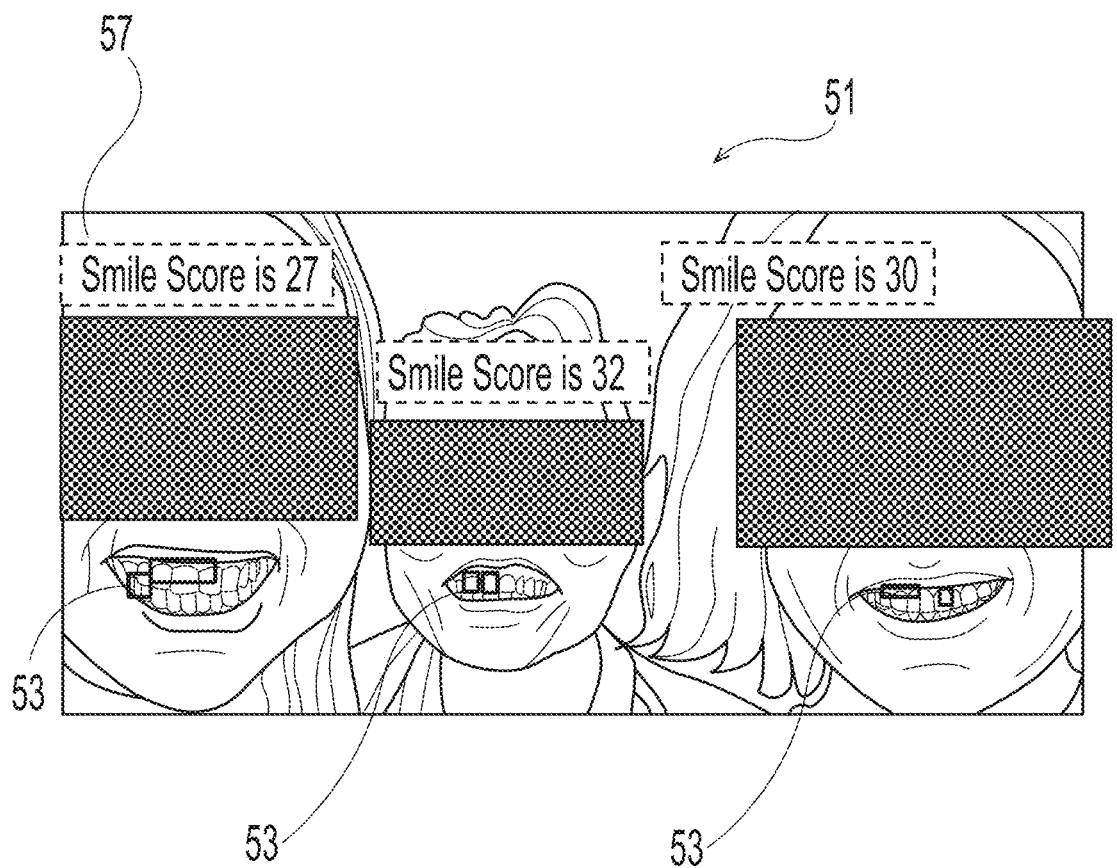
FIG. 21 is a screen shot illustrating an exemplary presentation of an image description for a facial image portion of a plurality of persons.

FIG. 21 is a screen shot of a digital image 51 of a plurality of persons wherein an image description 53 is presented for each detected facial image portion 52 for each of the plurality of persons. As shown in FIG. 3, the detected facial image portion 52 is a smile 521 and an Attractiveness Score 57 is presented visually in the digital image 51. The Attractiveness Score 57 may include but is not limited to a numerical value indicative of perceived attractiveness of the smile 521 relative to a population of people. The Attractiveness Score 57 may be a smile score for the smile 521.

Training Dataset

For example, the CNN model described hereinbefore may be trained and evaluated by a dataset of simulated teeth images.

A training dataset of simulated teeth images ("Simulated Images Dataset") may be built as described hereinafter for defining the Attractiveness Score. The training dataset design criteria may be based on eight different teeth attributes as described in Table 4 below, and different score levels ranging from 0% to 100% are assigned to each set of images belong to the same teeth attribute.

TABLE 4

| | Oral Feature Attribute | Level1 | Level2 | Level3 | Level4 | Level5 |
|---|---|---|---|---|---|---|
| 1 | Lightness | 20% | 40% | 60% | 80% | 100% |
| 2 | Yellowness | 20% | 30% | 40% | 50% | 60% |
| 3 | Opacity | 20% | 40% | 60% | 80% | 100% |
| 4 | Facial Staining | 20% | 40% | 60% | 80% | 100% |
| 5 | Shine | 20% | 40% | 60% | 80% | 100% |
| 6 | Interproximal (IP) Staining | 20% | 40% | 60% | 80% | 100% |
| 7 | Marginal Staining | 20% | 40% | 60% | 80% | 100% |
| 8 | Gum Redness | 20% | 40% | 60% | 80% | 100% |

There may be a set of simulated images for facial staining, each simulated image corresponding to a different score level. The preparation of the simulated images is based on an assumption that a simulated image corresponding to a lower score has a predetermined area of front teeth surfaces having facial staining (negative attribute) and a larger area of white front teeth surfaces (positive attribute) and will be deemed to be more attractive relative to another image having the same predetermined area of front teeth surfaces but corresponding to a higher score. The predetermined area of the facial staining is the same from low to high scores, but the color intensity of the facial staining in different images increases from low to high scores.

A set of three different images may be shown side by side to consumers represent combinations of all eight attributes. For each image, the particular level of the eight attributes was determined by a balanced, designed, discrete choice (conjoint) randomization. So, within each choice set, up to all eight attributes' levels differed among the three images according to the randomization. This was to determine what they really perceived as most attractive.

For example, when a consumer may be shown a given set of three images, and the three images may be made of any combination of the set of attributes below, including facial staining, with a given level of each attribute represented in each set of teeth.

An attractiveness model based on the training data may be obtained from the raw consumer choice data by estimating the part-worth utilities for the eight attributes' main effects and limited interaction terms via hierarchical bayes (HB) estimation. The Attractiveness Score for any particular training image could then be calculated from the sum of the part-worth utilities across the chosen attribute levels.

The Simulated Images Dataset can be modified in the same way based on knowing which skin attributes to define, e.g. pigmentation, or other skin attributes, and that can be built into the Attractiveness model and analysed accordingly. For example, if the facial image portion is skin, a Simulated Images Dataset may be generated by modifying skin images based on the dataset design criteria described hereinbefore for teeth and then applied to the Attractiveness model for determining attractiveness of skin.

An advantage of the Simulated Images Dataset is that it is easy to define a level of measure for attributes that are relevant to the consumer and thereby gain a better and controllable measure of the attributes that is driving their perception of attractiveness. Use of simulated images provides an advantage of using data that is consumer relevant to generate the score, therefore the score is consumer relevant and is not a random result generated from random stock facial images.

As each and every image that is consumer relevant can be classified and labelled, thereby use of the Simulated Images Dataset for training a machine model will enable the machine model to generate consumer relevant results.

Alternatively, a predetermined population size of real people images may be gathered to build a training dataset based on the predetermined population of real people, and a discrete choice model may be used to estimate the attractiveness of the facial image portion.

In an exemplary example, a process for building a training dataset may comprise the following steps:
(1) Create attribute images
(2) Randomize them in a design
(3) Collect consumer discrete choice data
(4) Estimate attribute image utilities as training data
(5) Build machine learning algorithm based on training data utility scores The training data set can be created for any system that can be broken down into bodily attributes and their levels. Discrete choice models may be used to describe the attributes. Preferably, the discrete choice model is conjoint statistics which may be used to describe combinations of fixed (controlled) attributes. Alternatively, the discrete choice model may be MaxDiff analysis which may be used to describe collections of non-fixed (uncontrolled) attribute images (e.g. a large set of clinical images) that have known scores for the attribute levels identified (e.g. clinical grading for staining, yellowness or any desired oral feature attribute).

Further, consumers may interpret attractiveness of one or more oral features and as such, the term "attractiveness" may have multiple words used for the image description that is displayed in the step (e) presenting 210 the image description 53 to a user according to the present invention. Table 5 below is a non-exhaustive list of consumer relevant descriptions that may be used for the image description is described below relative to the relevant facial image portion, specifically, oral feature attributes.

TABLE 5

Consumer Relevant Descriptions for Perceived Attractiveness of Oral Feature Attributes-English (Chinese)

| Oral Feature Gum | Oral Feature Teeth | Facial Expression Smile |
|---|---|---|
| Healthy(健康) | shiny/glossy(闪亮/闪耀) | Attractive or appealing (有吸引力/动人的) |
| Pink/Pink &Tender (粉嫩/粉红) flexibility and resilience or terms describing gum texture properties (柔韧/坚韧/弹力) firm (紧实/紧致) | brightness from the whiteness (白里透光) hydrated whitening (水光白) | affinitive/easy-going(有亲和力) appealingly/with strong influence power (的有感染力) |
|  | shiny whitening (亮白/莹白) | purely/naturally (纯真/纯粹/自然/单纯) |
| Aligned and fitting with teeth (贴合) | naturally white without any 'makeup' like face without makeup (素颜白) | Sincerely(真诚地) |
| Plump(饱满) | cleansing whitening (净白/洁白) | sunny/lively or terms for describe young and cute girls(元气地) softly/gently(温柔地) |
| gingival stippling (有点彩) | celebrity/super model's shiny whitening (明星闪光白) |  |
| Hurt (痛) hot/warm (热) | pearl white(珍珠白) natural whitening/newborn whitening, i.e. as white as the teeth at birth (原生白/初生白) diamond white (钻白/晶钻白) white from inner to outside(由内而外白) Strong (坚固) Healthy (健康) | Warmly (温暖地) Confidently(自信地) |

Representative embodiments of the present disclosure described above can be described as set out in the following paragraphs:

A. An oral oral care based digital imaging computer-implemented method for determining perceived attractiveness of a facial image portion (52) of at least one person depicted in a digital image (51), the method comprising the steps of:
  a) Obtaining (202) a digital image (51) comprising at least one oral feature of at least one person, wherein the digital image (51) comprises a facial image portion (52) of the at least one person, wherein the facial image portion (52) has both positive and negative attributes as defined by pixel data of the digital image (51);
  b) Analyzing (204) the facial image portion (52);
  c) Generating (206) an Attractiveness Score (57) indicative of a perceived attractiveness of the facial image portion (52) based on the analyzed facial image portion (52) in the obtained digital image (51);
  d) Further generating (208) an image description (53) that identifies at least one area in said facial image portion (52) indicative of the Attractiveness Score (57); and
  e) Presenting (210) the image description (53) to a user.

B. The method method according to paragraph A, wherein the Attractiveness Score is generated as a probability value indicative of how appealing a facial image portion of a person depicted in a digital image is to a population of people based on positive and negative attributes of the facial image portion, preferably the probability value is determined by a model constructed by a machine learning system trained by a training dataset, wherein the training dataset comprises i) a plurality of simulated images of a facial image portion comprising positive and negative attributes; and (ii) an associated class definition based on positive and negative attributes.

C. The method method according to paragraph A or B, further comprising presenting the Attractiveness Score (57) to the user after step (c).

D. The method according to any one of paragraphs A-C, wherein the image description (53) further indicates the impact of said identified area in said facial image portion (52) on the Attractiveness Score (57).

E. The method according to any one of paragraphs A-D, wherein the facial image portion (52) is selected from the group consisting of: facial skin, one or more oral features, one or more facial expressions, and combinations thereof.

F. The method according to any one of paragraphs A-E, wherein the facial image portion (52) comprises one or more oral features selected from the group consisting of: oral cavity soft tissue, gum, teeth, and combinations thereof.

G. The method according to any one of paragraphs A-E, wherein the facial image portion (52) is a facial expression of the person, wherein the facial expression is a smile (521).

H. The method according to any one of paragraphs A-E, wherein the facial image portion is defined by a first oral feature and a second oral feature associated with the facial image portion, each of the first and second oral features is selected from the group consisting of: oral cavity soft tissue, gum, teeth, and combinations thereof.

I. The method according to paragraph H, wherein the first oral feature comprises a first set of characteristics indicative of positive cosmetic dental attributes for the facial image portion (52), each positive cosmetic dental attribute is assigned a positive value indicative that the first oral feature is healthy; wherein the second oral feature comprises a second set of characteristics indicative of negative cosmetic dental attributes for the facial image portion (52), wherein the first oral feature and the second oral feature are located in different parts of the at least one area in the facial image portion (52).

J. The method according to any one of paragraphs A-I, further comprising, detecting the facial image portion (52) in the obtained digital image prior to step (b).

K. The method according to any one of paragraphs A-J, wherein analyzing in step (b) comprises filtering the facial image portion (52) to obtain one or more filtered feature maps comprising a first feature of interest and a second feature of interest, each of the first and second features of interest is associated with the facial image portion (52); wherein the first feature of interest comprises a first set of characteristics indicative of positive attributes for the facial image portion (52), and the second feature of interest comprises a second set of characteristics indicative of negative attributes for the facial image portion (52), wherein the first feature of interest and the second feature of interest are located in different parts of the at least one area in the facial image portion.

L. The method according to any one of paragraphs A-K, wherein presenting the image description (53) comprises one of: displaying the image description (53) in the digital image (51) as alternative text (531), displaying the image description (53) in the digital image (51) as a heat map (532), providing the image description (53) for audible presentation to the user, and combinations thereof.

M. The method according to paragraph L, wherein displaying the image description (53) in the digital image (51) as a heat map (532) comprises generating the heat map (532), wherein generating the heat map comprises overlaying a layer on at least a portion of the digital image comprising the facial image portion, wherein the layer is a pixel map that identifies the at least one area comprising at least one of said analyzed positive and/or negative attributes.

N. The method according to any one of paragraphs A-M, further comprising receiving a request for additional information about the facial image portion (52); preferably the additional information comprises providing information related to improvement of the Attractiveness Score.

O. The method according to any one of paragraphs A-N, further comprising receiving a request to share the image description (53) to a second user.

P. The method according to any one of paragraphs A-O, wherein the image description (53) comprises a single face of a person depicted in the digital image (51).

Q. The method according to any one of paragraphs A-P, wherein the image description (53) comprises a plurality of faces of persons depicted in the digital image (51) and an individual image description (53) is presented for each of the plurality of faces of persons.

R. A method (400) for presenting a product recommendation for improving perceived attractiveness of a facial image portion, the method comprising:
transmitting a digital image (51) of at least one person, wherein the digital image comprises a facial image portion of the at least one person, wherein the facial image portion has both positive and negative attributes;
receiving an image presentation that identifies at least one area in the facial image portion comprising at least one of the negative attributes analysed using the method according to any one of paragraphs A-Q;
presenting a product recommendation for improving perceived attractiveness of the at least one of the analyzed positive and/or negative attributes.

S. A method of demonstrating efficacy of a customized oral care regimen in improving perceived attractiveness of one or more oral features of at least one person depicted in a digital image, the method comprising:
obtaining (202) a digital image (51) of the at least one person, wherein the digital image (51) comprises the one or more oral features of the at least one person, wherein the one or more oral features has both positive and negative attributes; wherein one or more oral features is treated with a customized oral care regimen;
determining perceived attractiveness of the one or more oral features using the method according to any one of paragraphs A-Q.

T. A method for demonstrating efficacy of a consumer product in improving perceived attractiveness of a facial image portion of at least one person depicted in a digital image, the method comprising:
i) Determining perceived attractiveness of a facial image portion (52) of a person in a first digital image (60) using the method according to any one of paragraphs A-Q; wherein the facial image portion (52) in the first digital image (60) is untreated;
ii) Obtaining a second digital image (61) of the person depicted in the first digital image (51), wherein the second digital image (61) comprises the facial image portion (52) of the person, wherein the facial image portion (52) in the second digital image (61) is treated with a consumer product for a treatment period;

iii) Further determining perceived attractiveness of the facial image portion (52) in the second digital image (61) using the method according to any one of paragraphs A-Q;

iv) Comparing perceived attractiveness of the facial image portion (52) in the second digital image (61) with perceived attractiveness of the facial image portion (52) in the first digital image (60).

U. The method according to paragraph T, wherein further comprising treating the facial image portion (52) in the first digital image (60) with a comparative consumer product after step (i) and prior to step (ii) based on the treatment period of step (ii).

V. The method according to paragraph T or V, wherein the treatment period is from two minutes to ten minutes, preferably two minutes to five minutes, more preferably three minutes.

W. The method according to any one of paragraphs T-V, further comprising repeating step (iii) and step (iv) over a period of time for tracking improvement in the perceived attractiveness of the facial image portion; wherein the period of time is from one day to three days, preferably from three days to seven days, more preferably from seven days to fourteen days.

X. A system (10) for determining perceived attractiveness of a facial image portion of at least one person depicted in a digital image, the system (10) comprising:
a mobile application capable of being compiled to run on a client computing system for obtaining a digital image comprising at least one oral feature of at least one person, wherein the digital image includes a facial image portion of the at least one person, wherein said computing system is in communication with a content server configured to store the obtained digital image;
an image processing device (14) in communication with the mobile application through a network (100); wherein said image processing device (14) comprises a processor (14b) configured to, based on computer-executable instructions stored in a memory (14a) to analyze the facial image portion, generate an Attractiveness Score indicative of the perceived attractiveness of the facial image portion based on the analyzed facial image portion in the obtained digital image; and further generating an image description that identifies at least one area in said facial image portion indicative of the Attractiveness Score;
a display generating unit for generating a display to display the image description indicative of the Attractiveness Score.

Y. An oral care based digital imaging method for providing information to graphical user interfaces for improving perceived attractiveness of a facial image portion of at least one person depicted in a digital image, the oral care based digital imaging method comprising:
implementing a graphical user interface (30) on a portable electronic apparatus including a touch screen display or a display with an input device and an image obtaining device for obtaining a digital image comprising at least one oral feature of at least one person, wherein the digital image includes a facial image portion of the at least one person;
displaying, on a first area of the display, an image description (53) that identifies at least one area in said facial image portion indicative of an Attractiveness Score;
displaying, on a second area of the display different from the first area, a selectable icon (54) for receiving a user input; and sending, upon selection of the selectable icon (54) and by a network interface digitally coupling the apparatus to an image processing device, a request for additional information about the facial image portion (52), wherein the additional information is related to improvement of the Attractiveness Score.

Z. The method of paragraph R further comprising:
receiving a selection corresponding to the product recommendation; and
performing at least one of the following based on the selection: (1) preparing a product for shipment corresponding to the product recommendation, or (2) shipping the product to a physical address.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care digital imaging computer-implemented method for determining perceived attractiveness of a facial image portion of at least one person depicted in a digital image, the method comprising the steps of:
a) obtaining the digital image comprising at least one oral feature of the at least one person, wherein the digital image comprises the facial image portion of the at least one person, wherein the facial image portion has both positive and negative attributes as defined by pixel data of the digital image;
b) analyzing the facial image portion;
c) generating an Attractiveness Score indicative of a perceived attractiveness of the facial image portion based on the analyzed facial image portion in the obtained digital image, wherein the Attractiveness Score is generated as a probability value indicative of how appealing the facial image portion of the at least one person depicted in a digital image is to a population of people based on the positive and negative attributes of the facial image portion, wherein the probability value is determined by a model constructed by a machine learning system trained by a training dataset, and wherein the training dataset comprises (i) a plurality of simulated images of a facial image portion comprising simulated positive and negative attributes; and (ii) an associated class definition based on the simulated positive and negative attributes;
d) further generating an image description that identifies at least one area in the facial image portion based on the Attractiveness Score; and
e) presenting the image description to a user.

2. The method of claim 1, wherein the method comprises presenting the Attractiveness Score to the user after step (c).

3. The method of claim 1, wherein the image description further indicates an impact of the identified area in the facial image portion on the Attractiveness Score, wherein the image description comprises a consumer relevant description for perceived attractiveness of the facial image portion.

4. The method of claim 1, wherein the facial image portion comprises facial skin, one or more oral features, one or more facial expressions, or combinations thereof.

5. The method of claim 4, wherein the facial image portion comprises the one or more oral features, and the one or more oral features comprises oral cavity soft tissue, gum, teeth, or combinations thereof.

6. The method of claim 4, wherein the facial image portion comprises the one or more facial expressions, and the one or more facial expressions comprises a smile.

7. The method of claim 1, wherein the facial image portion is defined by a first oral feature and a second oral feature associated with the facial image portion, each of the first oral feature and the second oral feature comprising oral cavity soft tissue, gum, teeth, or combinations thereof.

8. The method according to claim 7, wherein the first oral feature comprises a first set of characteristics indicative of positive cosmetic dental attributes for the facial image portion, each positive cosmetic dental attribute is assigned a positive value indicative that the first oral feature is healthy; wherein the second oral feature comprises a second set of characteristics indicative of negative cosmetic dental attributes for the facial image portion, wherein the first oral feature and the second oral feature are located in different parts of the at least one area in the facial image portion.

9. The method of claim 1, wherein the method comprises receiving a request for additional information about the facial image portion, wherein the additional information comprises providing information related to improvement of the Attractiveness Score.

10. The method of claim 1, wherein analyzing in step (b) comprises filtering the facial image portion to obtain one or more filtered feature maps comprising a first feature of interest and a second feature of interest, each of the first and second features of interest is associated with the facial image portion, wherein the first feature of interest comprises a first set of characteristics indicative of positive attributes for the facial image portion, and the second feature of interest comprises a second set of characteristics indicative of negative attributes for the facial image portion, and wherein the first feature of interest and the second feature of interest are located in different parts of the at least one area in the facial image portion.

11. The method of claim 1, wherein presenting the image description comprises displaying the image description in the digital image as alternative text, displaying the image description in the digital image as a heat map, providing the image description for audible presentation to the user, or combinations thereof.

12. The method of claim 11, wherein presenting the image description comprises displaying the image description in the digital image as the heat map, and displaying the image description in the digital image as the heat map comprises generating the heat map.

13. The method of claim 12, wherein generating the heat map comprises overlaying a layer on at least a portion of the digital image comprising the facial image portion.

14. The method of claim 13, wherein the layer is a pixel map that identifies the at least one area comprising at least one of the analyzed positive and/or negative attributes.

15. A method for presenting a product recommendation for improving perceived attractiveness of a facial image portion, the method comprising:
transmitting the digital image of claim 1;
receiving an image presentation that identifies at least one area in the facial image portion comprising at least one of the negative attributes analyzed using the method of claim 1; and
presenting a product recommendation for improving perceived attractiveness of the at least one of the analyzed positive and/or negative attributes.

16. A method of demonstrating efficacy of a customized oral care regimen in improving perceived attractiveness of one or more oral features of at least one person depicted in a digital image, the method comprising:
obtaining a digital image of the at least one person, wherein the digital image comprises the one or more oral features of the at least one person, wherein the one or more oral features has both positive and negative attributes and wherein the one or more oral features is treated with a customized oral care regimen; and
determining perceived attractiveness of the one or more oral features using the method of claim 1.

17. A method for demonstrating efficacy of a consumer product in improving perceived attractiveness of a facial image portion of at least one person depicted in a digital image, the method comprising:
i) determining perceived attractiveness of a facial image portion of a person in a first digital image using the method of claim 1, wherein the facial image portion in the first digital image is untreated;
ii) obtaining a second digital image of the person depicted in the first digital image, wherein the second digital image comprises the facial image portion of the person, wherein the facial image portion in the second digital image is treated with a consumer product for a treatment period;
iii) further determining perceived attractiveness of the facial image portion in the second digital image using the method of claim 1; and
iv) comparing perceived attractiveness of the facial image portion in the second digital image with perceived attractiveness of the facial image portion in the first digital image.

18. The method according to claim 17, wherein further comprising treating the facial image portion in the first digital image with a comparative consumer product after step (i) and prior to step (ii) based on the treatment period of step (ii) wherein the treatment period is from two minutes to ten minutes.

19. The method of claim 17, further comprising repeating step (iii) and step (iv) over a period of time for tracking improvement in the perceived attractiveness of the facial image portion, wherein the period of time is from one day to fourteen days.

20. The method of claim 18, wherein the perceived attractiveness of the facial image portion is teeth whitening.

21. A system for determining perceived attractiveness of a facial image portion of at least one person depicted in a digital image, the system comprising:
a mobile application capable of being compiled to run on a client computing system for obtaining a digital image comprising at least one oral feature of at least one person, wherein the digital image includes a facial image portion of the at least one person, wherein the computing system is in communication with a content server configured to store the obtained digital image;
an image processing device in communication with the mobile application through a network; wherein the image processing device comprises a processor configured to, based on computer-executable instructions stored in a memory to analyze the facial image portion, generate an Attractiveness Score indicative of the perceived attractiveness of the facial image portion based on the analyzed facial image portion in the obtained digital image; and further generating an image description that identifies at least one area in the facial image portion indicative of the Attractiveness Score; and
a display generating unit for generating a display to display the image description indicative of the Attractiveness Score,
wherein the Attractiveness Score is generated as a probability value indicative of how appealing the facial image portion of the at least one person depicted in a digital image is to a population of people based on positive and negative attributes of the facial image portion, wherein the probability value is determined by a model constructed by a machine learning system trained by a training dataset, and wherein the training dataset comprises (i) a plurality of simulated images of a facial image portion comprising simulated positive and negative attributes; and (ii) an associated class definition based on the simulated positive and negative attributes.

22. An oral care based digital imaging method for providing information to graphical user interfaces for improving perceived attractiveness of a facial image portion of at least one person depicted in a digital image, the oral care based digital imaging method comprising:
implementing a graphical user interface on a portable electronic apparatus, the portable electronic apparatus including a touch screen display or a display with an input device and an image obtaining device for obtaining a digital image comprising at least one oral feature of at least one person, wherein the digital image includes the facial image portion of the at least one person;
displaying, on a first area of the display, an image description that identifies at least one area in the facial image portion indicative of an Attractiveness Score, wherein the Attractiveness Score is generated as a probability value indicative of how appealing the facial image portion of the at least one person depicted in a digital image is to a population of people based on the positive and negative attributes of the facial image portion, wherein the probability value is determined by a model constructed by a machine learning system trained by a training dataset, and wherein the training dataset comprises (i) a plurality of simulated images of a facial image portion comprising simulated positive and negative attributes; and (ii) an associated class definition based on the simulated positive and negative attributes;
displaying, on a second area of the display different from the first area, a selectable icon for receiving a user input; and
sending, upon selection of the selectable icon and by a network interface digitally coupling the apparatus to an image processing device, a request for additional information about the facial image portion, wherein the additional information is related to improvement of the Attractiveness Score.

23. The method of claim 19, wherein the method comprises:
receiving a selection corresponding to the product recommendation; and
performing at least one of the following based on the selection: (1) preparing a product for shipment corresponding to the product recommendation, or (2) shipping the product to a physical address.

* * * * *

UNITED STATES PATENT AND TRADEMARK OFFICE
CERTIFICATE OF CORRECTION

| | |
|---|---|
| PATENT NO. | : 11,978,207 B2 |
| APPLICATION NO. | : 17/337503 |
| DATED | : May 7, 2024 |
| INVENTOR(S) | : Amirhossein Tavanei et al. |

It is certified that error appears in the above-identified patent and that said Letters Patent is hereby corrected as shown below:

On the Title Page

Insert the following, before Item (51) Int. Cl.:
-- (30) Foreign Application Priority Data
Jun. 4, 2020 (CN) PCT/CN2020/094342 --

Signed and Sealed this
Fourth Day of June, 2024

Katherine Kelly Vidal
*Director of the United States Patent and Trademark Office*